United States Patent
Hernandez et al.

(10) Patent No.: US 12,156,921 B2
(45) Date of Patent: *Dec. 3, 2024

(54) PSMA-TARGETING LIGANDS WITH OPTIMAL PROPERTIES FOR IMAGING AND THERAPY

(71) Applicant: Wisconsin Alumni Research Foundation, Madison, WI (US)

(72) Inventors: Reinier Hernandez, Madison, WI (US); Anatoly Pinchuk, Fitchburg, WI (US)

(73) Assignee: Wisconsin Alumni Research Foundation, Madison, WI (US)

(*) Notice: Subject to any disclaimer, the term of this patent is extended or adjusted under 35 U.S.C. 154(b) by 0 days.

This patent is subject to a terminal disclaimer.

(21) Appl. No.: 18/303,708

(22) Filed: Apr. 20, 2023

(65) Prior Publication Data
US 2023/0302164 A1    Sep. 28, 2023

Related U.S. Application Data

(63) Continuation of application No. 18/161,395, filed on Jan. 30, 2023, which is a continuation of application No. PCT/US2022/025978, filed on Apr. 22, 2022.

(60) Provisional application No. 63/178,566, filed on Apr. 23, 2021.

(51) Int. Cl.
*A61K 51/04* (2006.01)
*A61P 13/08* (2006.01)
*A61P 35/00* (2006.01)

(52) U.S. Cl.
CPC ......... *A61K 51/0497* (2013.01); *A61P 13/08* (2018.01); *A61P 35/00* (2018.01)

(58) Field of Classification Search
CPC ........... A61K 51/04; A61P 13/08; A61P 35/00
See application file for complete search history.

(56) References Cited

U.S. PATENT DOCUMENTS

| | | | |
|---|---|---|---|
| 6,045,821 A | 4/2000 | Garrity | |
| 8,211,401 B2 * | 7/2012 | Babich | A61P 25/18 424/1.65 |
| 9,694,091 B2 | 7/2017 | Pomper et al. | |
| 10,265,398 B2 | 4/2019 | Weichert | |
| 10,813,998 B2 | 10/2020 | Weichert | |
| 11,186,598 B2 | 11/2021 | Weichert | |
| 2007/0292354 A1 | 12/2007 | Port | |
| 2010/0284929 A1 | 11/2010 | Pinchuk et al. | |
| 2010/0284931 A1 | 11/2010 | Pinchuk et al. | |
| 2014/0030187 A1 | 1/2014 | Weichert | |
| 2016/0296646 A1 | 10/2016 | Weichert | |
| 2019/0336622 A1 | 11/2019 | Eder et al. | |
| 2021/0015949 A1 | 1/2021 | Ferro Flores et al. | |

FOREIGN PATENT DOCUMENTS

| | | | |
|---|---|---|---|
| WO | 2005/084716 | 9/2005 | |
| WO | WO-2009026177 A1 * | 2/2009 | ........... A61K 31/426 |
| WO | 2009/027706 | 3/2009 | |
| WO | 2010/144788 | 12/2010 | |
| WO | 2016/081203 | 5/2016 | |
| WO | 2021/041896 A1 | 3/2021 | |

OTHER PUBLICATIONS

Pubchem, SID 344116250, 2017, 8 pages, retrieved from the Internet URL:https://pubchem.ncbi.nlm.nih.gov/substance/344116250.
Weichert et al, "Alkylphosphocholine Analogs for Broad-Spectrum Cancer Imaging and Therapy" Science Translational Medicine, vol. 6, No. 240, Jun. 11, 2014, pp. 1-10 (Exhibit 2).
Cai et al, "Chelators for copper radionuclides in positron emission tomography radiopharmaceuticals" J. Label Compd. Radiopharm 2014, 57, pp. 224-230 (Exhibit 7).
Deri, Melissa A., et al., "PET imaging with 89Zr: From radiochemistry to the clinic," Nuclear Medicine and Biology, vol. 40, No. 1, 2013, pp. 3-14.
International Search Report and Written Opinion dated Apr. 19, 2017, International Patent Application No. PCT/US2016/060495.
Mueller, Cristina, et al., "Folate Receptor-Targeted Radionuclide Imaging Agents", 2011, Targeted Drug Strategies or Cancer and Inflammation, pp. 65-92.
Brechbiel et al, "Bifunctional Chelates for Metal Nuclides" Q J Nucl Med Mol Imaging, HHS Public Access Author manuscript; available in PMC Jun. 9, 2009, pp. 1-17, PMCID: PMC2693392 (Exhibit 6).
Request for Reexamination of U.S. Pat. No. 11,186,598 issued Nov. 30, 2021 to Weichert et al., entitled "Radioactive phospholipid metal chelates for cancer imaging and therapy".

(Continued)

*Primary Examiner* — Michael G. Hartley
*Assistant Examiner* — Jagadishwar R Samala
(74) *Attorney, Agent, or Firm* — McDonnell Boehnen Hulbert & Berghoff LLP

(57) ABSTRACT

Theranostic agents incorporating a chelating moiety that can chelate a radioactive metal isotope and a PSMA-targeting moiety are disclosed herein. The theranostic agents, which can be used to treat and/or detect cancers associated with increased PSMA expression, have the formula:

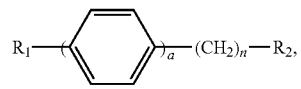

and include complexes, anions or salts thereof. $R_1$ includes a chelating moiety; a is 0 or 1; n is an integer from 12 to 21; and $R_2$ includes a prostate specific membrane antigen (PSMA)-targeting moiety. Optionally, the chelating moiety is chelated to a metal atom, where the metal atom is a positron or single photon emitting metal isotope, or an alpha, beta, or Auger emitting metal isotope.

11 Claims, 8 Drawing Sheets

(56) References Cited

OTHER PUBLICATIONS

Fonge et al, "Influence of formulation variables on the biodistribution of multifunctional block copolymer micelles" Journal of Controlled Release 157 (2012) pp. 366-374 (Exhibit 4).

* cited by examiner

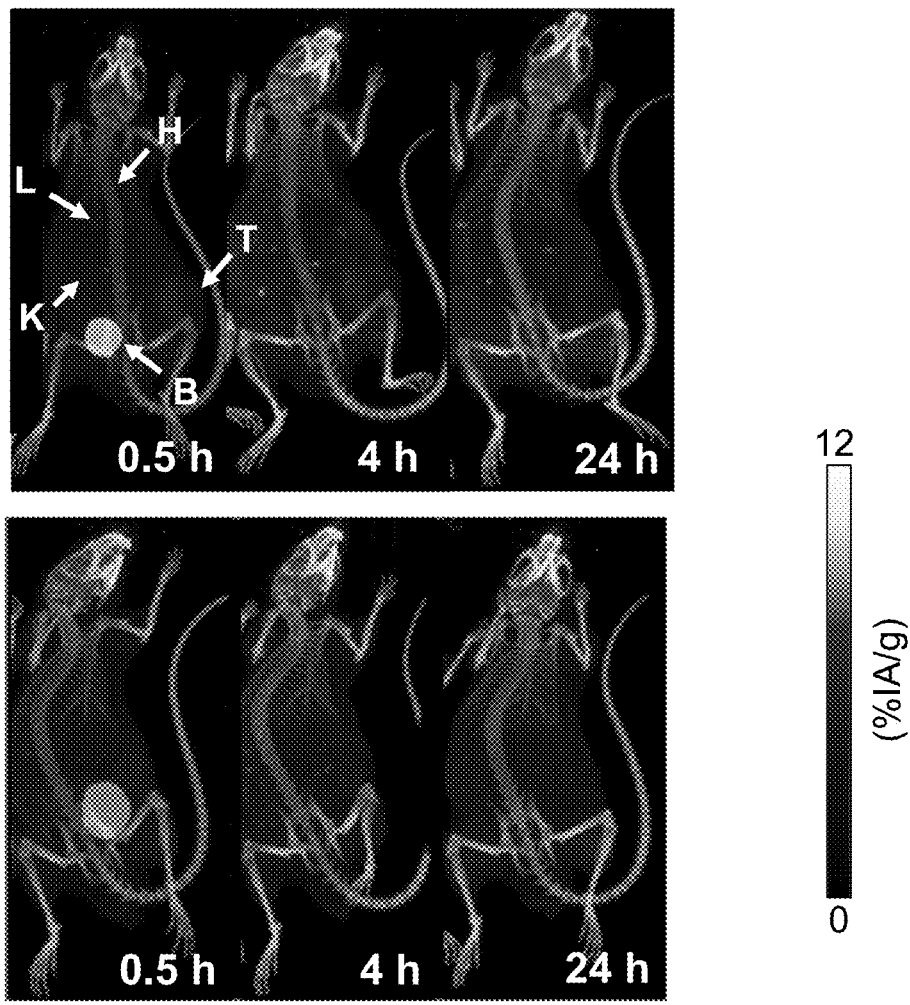
FIG. 4A
FIG. 4B
FIG. 4C

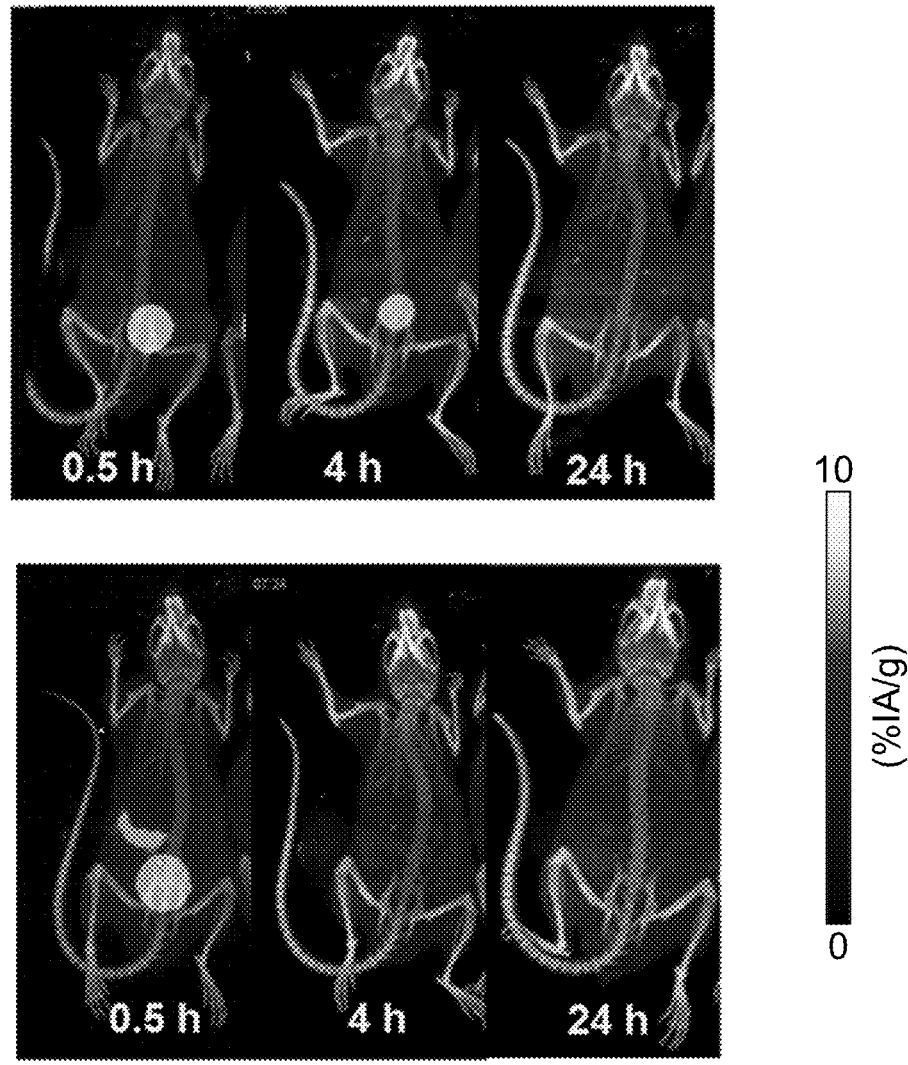
FIG. 7A
FIG. 7B
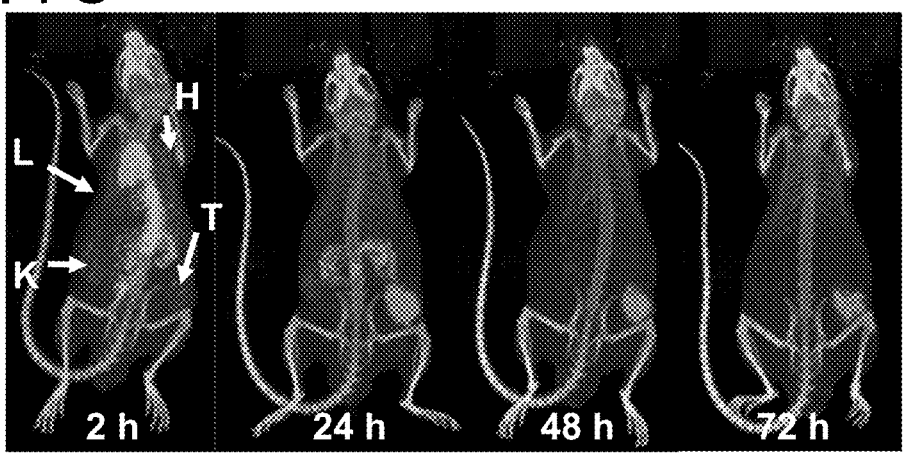
FIG. 7C

PSMA-TARGETING LIGANDS WITH OPTIMAL PROPERTIES FOR IMAGING AND THERAPY

CROSS-REFERENCE TO RELATED APPLICATIONS

This application is a continuation of U.S. patent application Ser. No. 18/161,395, filed on Jan. 30, 2023, which is a continuation of International Application No. PCT/US2022/025978, filed on Apr. 22, 2022, which claims priority to U.S. Provisional Application No. 63/178,566, filed on Apr. 23, 2021, which are incorporated herein by reference in their entirety.

STATEMENT REGARDING FEDERALLY SPONSORED RESEARCH OR DEVELOPMENT

Not applicable.

FIELD OF THE DISCLOSURE

This disclosure relates generally to disease treatment and medical diagnosis/imaging. In particular, the disclosure is directed to prostate specific membrane antigen (PSMA)-targeting theranostic agents that may optimally include chelated radioactive metal isotopes to target and treat prostate cancer, and to detect/image prostate cancer.

BACKGROUND

"Theranostics," a term derived from a combination of therapeutics and diagnostics, is an emerging field of medicine where specific disease-targeting agents may be used to simultaneously or sequentially diagnose and treat medical conditions. Theranostics has become an important field of research and development in medical physics, where varying the isotope of the radionuclide present in a given disease-targeting agent can change the disease-targeting agent from an imaging probe (by, e.g., using $\beta^+$ or $\gamma$ emitting isotopes to facilitate positron emission tomography (PET) or single photon emission computed tomography (CT) imaging, respectively), to a therapy probe (by, e.g., using a or $\beta^-$ particle or Auger electron emitting isotopes to facilitate targeted radiotherapy).

Prostate specific membrane antigen (PSMA) can be overexpressed in metastatic cancer (such as, but not limited to, prostate cancer) relative to normal tissue, and radionuclide tracers specific for PSMA have been developed for PET imaging and for targeted radiotherapy. For example, a PSMA-targeting moiety containing a Glu-urea-Lys PSMA binding motif has been linked to various metal chelators (e.g., DOTA, NOTA) to produce ligands such as PSMA-11, PSMA-617, PSMA-R2, and PSMA I&T. These ligands can potentially be chelated with an appropriate radionuclide for specific theranostic applications.

While a number of such ligands are known in the art for the targeting of PSMA, these ligands have a number of significant shortcomings. Specifically, they exhibit relatively short blood circulation half-lives and poor tumor retention. Furthermore, they exhibit significant off-target binding, and are differentially retained in both salivary gland and kidney tissue. In addition, these known ligands are excreted renally (with little or no hepatic excretion), are generally administered along with one or more albumin binders, and exhibit less than ideal bioavailability. Accordingly, there is a need in the art for improved cancer-targeting theranostic agents for use in radiation therapy and/or imaging applications that do not have these shortcomings.

A further consideration for known PSMA-targeting ligands is the suitability of the ligands for targeted radiotherapy using $\alpha$ or Auger electron emitters. Different types of emitted particles for radiotherapy (e.g., $\alpha$ or $\beta^-$ particles or Auger electrons) have different linear energy transfers (LET), which determine the effective dose per distance for each particle type. The higher the LET, the more radioactive dose is deposited to a given region. Because alpha particles and Auger electrons have high LETs, for effective treatment, the ligands used to deliver radionuclides emitting such particles must deliver the radionuclide as close to the target as possible. However, known ligands are not optimized for this, making them inadequate for targeted radiotherapy delivered by $\alpha$ or Auger electron emitters.

Accordingly, there is a further need in the art for improved cancer-targeting theranostic agents for use in radiation therapy that are optimized for use with a or Auger electron emitters.

BRIEF SUMMARY

The current disclosure provides new theranostic agents and radioactive metal chelates for cancer imaging and/or radiotherapy. A variety of positron- and gamma-emitting metals suitable for PET or SPECT imaging are available for chelation, as well as a variety of $\alpha$-, $\beta$-, and Auger-emitting metal nuclides for targeted radiotherapy.

The theranostic agents disclosed herein utilize a PSMA-targeting moiety combined with one of a variety of metal chelating moieties that can optionally be chelated to a radioactive metal isotope. The pharmacokinetics and related properties of the theranostic agents can be tuned and optimized by modifying the structure of the linker between the PSMA-targeting moiety and the metal chelating moiety.

Specifically, to tune the pharmacokinetics of the theranostic agents, the length of the carbon chain of the linker was modified, thus changing the hydrophobicity of the theranostic agent. The effect of changing the hydrophobicity of the theranostic agents on pharmacokinetics was also investigated—the longer the carbon chain, the more hydrophobic, and the longer the circulation half-life. The disclosed theranostics overall exhibit longer circulation half-life, bioavailability, and fewer off-target targeting properties as compared to known ligands. Furthermore, the excretion route of the theranostic can be tuned, increased hydrophobicity correlated with increased hepatic excretion (and decreased renal excretion). Finally, the disclosed theranostic agents can be optimized for specific use with targeted alpha-based radiotherapy.

The disclosed theranostic agents bind preferentially to cancer cells that have increased PSMA expression, as compared to normal cells. Accordingly, these agents can be used in the therapeutic treatment of prostate and other cancers associated with increased PSMA expression, as well as in cancer detection/imaging applications. In therapeutic treatment, the theranostic agent includes a chelated radioactive metal isotope that locally delivers therapeutic dosages of radiation to the cancer cells. In detection/imaging applications, the theranostic agent includes a chelated radioactive metal isotope suitable for emitting signals that can be used in detection/imaging.

Accordingly, this disclosure encompasses a family of theranostic agents that can be used as cancer imaging agents and/or therapeutic agents for targeted cancer radiotherapy.

In a first aspect, this disclosure encompasses theranostic agents having the formula:

$$R_1-(-\hspace{-0.3em}\langle\hspace{-0.3em}\rangle\hspace{-0.3em}-)_a-(CH_2)_n-R_2,$$

along with complexes, anions or salts of this formula. $R_1$ includes a chelating moiety, a is 0 or 1, n is an integer from 12 to 21, and $R_2$ includes a prostate specific membrane antigen (PSMA)-targeting moiety.

In some embodiments, n is 12.
In some embodiments, n is 13.
In some embodiments, n is 14.
In some embodiments, n is 15.
In some embodiments, n is 16.
In some embodiments, n is 17.
In some embodiments, n is 18.
In some embodiments, n is 19.
In some embodiments, n is 20.
In some embodiments, n is 21.

In some embodiments, the theranostic agent is more hydrophobic than PSMA-11, PSMA-617, PSMA-R2, EB-PSMA, or PSMA I&T.

In some embodiments, the theranostic agent is retained within a subject to which it is administered for a longer period of time than PSMA-11, PSMA-617, PSMA-R2, EB-PSMA, or PSMA I&T.

In some embodiments, the theranostic agent remains bound to prostate cancer cells within a subject to which it is administered for a longer period of time than PSMA-11, PSMA-617, PSMA-R2, EB-PSMA, or PSMA I&T.

In some embodiments, the theranostic agent has greater bioavailability within a subject to which it is administered than PSMA-11, PSMA-617, PSMA-R2, EB-PSMA, or PSMA I&T.

In some embodiments, the theranostic agent is excreted hepatically from a subject to which it is administered to a greater extent (and eliminated renally to a lesser extent) than PSMA-11, PSMA-617, PSMA-R2, EB-PSMA, or PSMA I&T.

In some embodiments, the theranostic agent binds to the salivary gland tissue of a subject to which it is administered to a lesser extent than PSMA-11, PSMA-617, or PSMA I&T.

In some embodiments, the theranostic agent binds to kidney tissue of a subject to which it is administered to a lesser extent than PSMA-11, PSMA-617, PSMA-R2, EB-PSMA, or PSMA I&T.

In some embodiments, the chelating moiety is chelated to a metal atom. In some such embodiments, the metal atom is in the form of a metal cation. In some such embodiments, the chelating moiety is anionic and selected such that the theranostic agent as a whole is electrically neutral.

In some embodiments, the metal atom is a positron or single photon emitting metal isotope, or an alpha, beta, or Auger emitting metal isotope.

In some embodiments, the metal atom is a positron or single photon emitting metal isotope. Such isotopes are particularly suited for use in imaging applications. Non-limiting examples of such isotopes include Ga-66, Cu-64, Y-86, Co-55, Zr-89, Sr-83, Mn-52, As-72, Sc-44, Sc-43, Ti-45, Tb-152, La-132, La-133, Ce-134, Ga-67, In-111, or Sm-153, Lu-177 or Tc-99m.

In some embodiments, the metal atom is an alpha, beta, or Auger emitting metal isotope. Such isotopes are particularly suited for use in targeted radiotherapy applications. Non-limiting examples of such metal isotopes include Lu-177, Y-90, Ho-166, Re-186, Re-188, Cu-67, Au-199, Rh-105, Ra-223, Ac-225, As-211, Pb-212, Sc-47, Sm-153, Tb-161, Tb-149, Bi-213, Bi-212, or Th-227.

In some embodiments, the chelating moiety is 1,4,7,10-tetraazacyclododecane-1,4,7-triacetic acid (DO3A) and its derivatives; 1,4,7-triazacyclononane-1,4-diacetic acid (NODA) or one of its derivatives; 1,4,7-triazacyclononane-1,4,7-triacetic acid (NOTA) or one of its derivatives; 1,4,7, 10-tetraazacyclododecane-1,4,7,10-tetraacetic acid (DOTA) or one of its derivatives; 1,4,7-triazacyclononane, 1-glutaric acid-4,7-diacetic acid (NODAGA) or one of its derivatives; 1,4,7,10-tetraazacyclodecane, 1-glutaric acid-4,7,10-triacetic acid (DOTAGA) or one of its derivatives; 1,4,8,11-tetraazacyclotetradecane-1,4,8,11-tetraacetic acid (TETA) or one of its derivatives; 1,4,8,11-tetraazabicyclo[6.6.2]hexadecane-4,11-diacetic acid (CB-TE2A) or one of its derivatives; diethylene triamine pentaacetic acid (DTPA), its diester, or one of its derivatives; 2-cyclohexyl diethylene triamine pentaacetic acid (CHX-A"-DTPA) or one of its derivatives; 2-(4-Isothicyanatobenzyl)-1,2,7,10,13-hexaaza-cyclooctadecane-1,4,7,10,13,16-hexaacetic acid (HEHA) or one of its derivatives; deforoxamine (DFO) or one of its derivatives; 1,2-[[6-carboxypyridin-2-yl]methylamino]ethane ($H_2$dedpa) or one of its derivatives; HOPO or one of its derivatives; MACROPA or one of its derivative; or DADA or one of its derivatives, where DADA has the structure:

In some embodiments, a is 1. In other embodiments, a is 0.

In some embodiments, $R_1$ is:

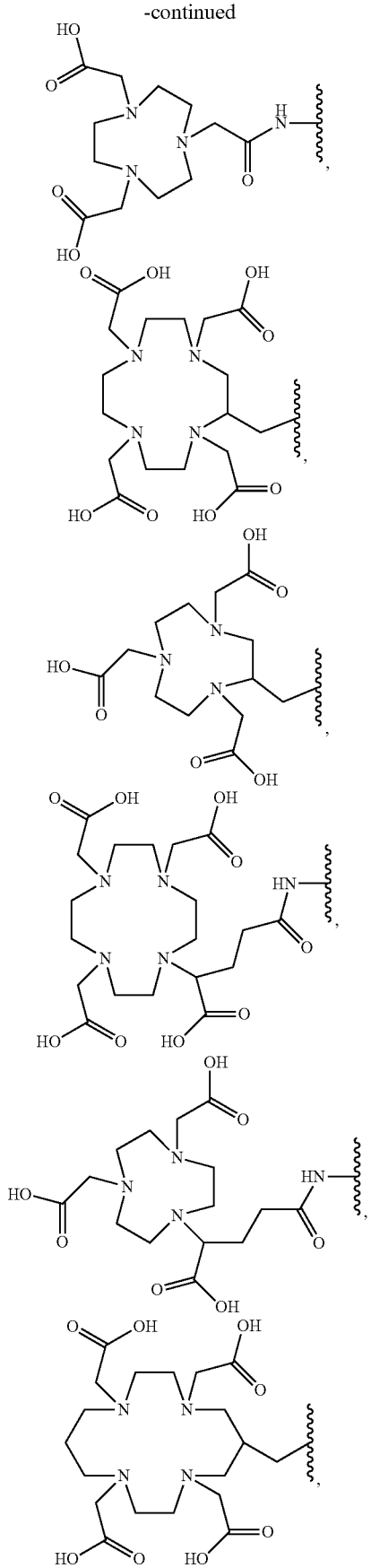
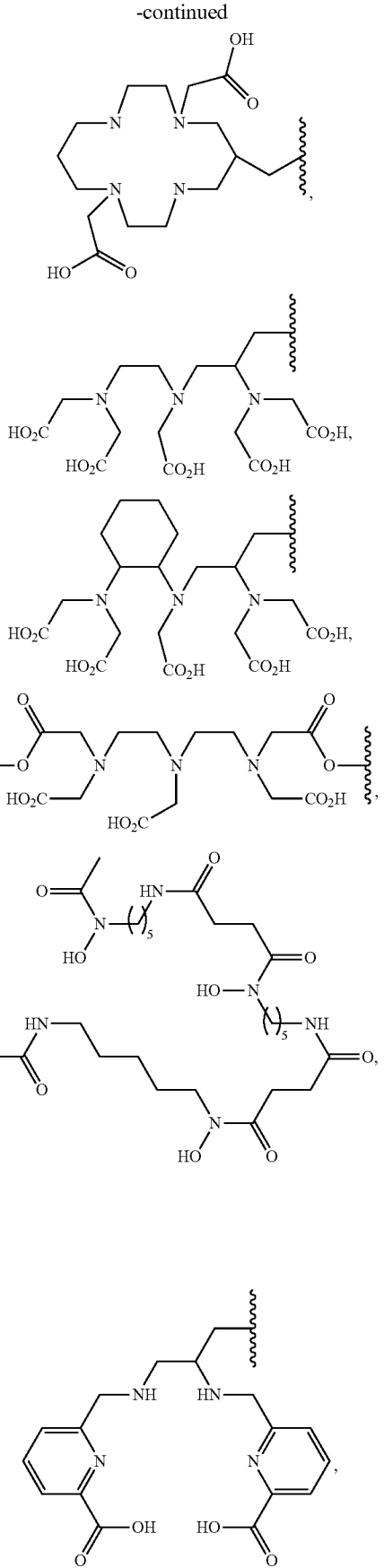

-continued

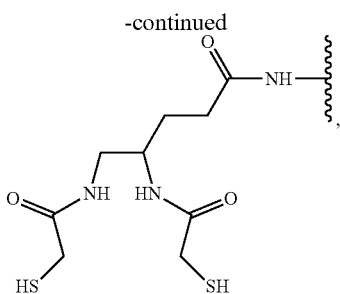

or any anions thereof.

In some embodiments, the PSMA-targeting moiety includes a urea-based PSMA-targeting moiety, a thiol-based PSMA-targeting moiety, or a phosphorus-based PSMA-binding moiety.

In some embodiments, the PSMA-targeting moiety includes a Glu-urea-Lys PSMA binding motif.

In some such embodiments, $R_2$ is:

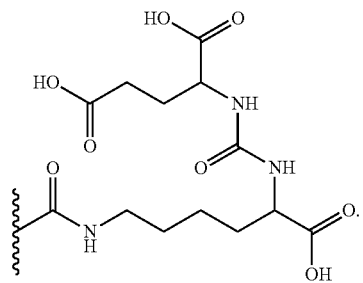 [SMILES: *C(=O)NCCCCC(NC(=O)NC(CCC(=O)O)C(=O)O)C(=O)O]

In some embodiments, the PSMA-targeting moiety includes a phosphoramidate PSMA-targeting moiety.

In some such embodiments, $R_2$ is:

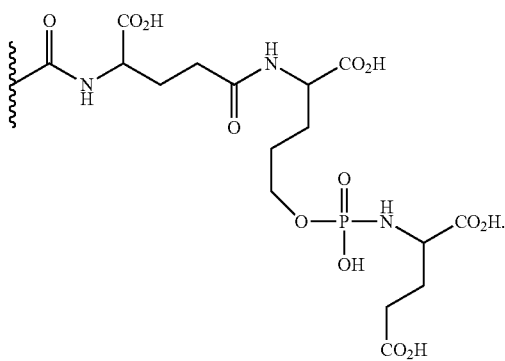 [SMILES: *C(=O)NC(CCC(=O)NC(CCCOP(=O)(O)NC(CCC(=O)O)C(=O)O)C(=O)O)C(=O)O]

In a second aspect, this disclosure encompasses a composition that includes the theranostic agent as described above, along with a pharmaceutically acceptable carrier. In some embodiments, the composition does not include an specific albumin binder.

In a third aspect, this disclosure encompasses a method for treating cancer associated with increased PSMA expression in a subject. The method includes the step of administering to a subject having cancer an effective amount of the theranostic agent as described above, where the theranostic agent includes a metal atom chelated to the chelating moiety, and where the metal atom is an alpha, beta, or Auger emitting metal isotope. As a result of performing this step, the cancer is successfully treated in the subject.

In some embodiments, the cancer that is treated is prostate cancer or breast cancer. In some embodiments, the cancer that is treated is prostate cancer.

In some embodiments, the metal isotope is Lu-177, Y-90, Ho-166, Re-186, Re-188, Cu-67, Au-199, Rh-105, Ra-223, Ac-225, As-211, Pb-212, Sc-47, Sm-153, Tb-161, Tb-149, Bi-213, Bi-212, or Th-227.

In some embodiments, the theranostic agent is administered in the absence of an albumen binder.

In some embodiments, the theranostic agent is administered by parenteral, intranasal, sublingual, rectal, or transdermal delivery. In some such embodiments, the theranostic agent is administered intravenously.

In some embodiments, the subject is a human.

In some embodiments, theranostic agent is retained within the subject to which it is administered for a longer period of time than PSMA-11, PSMA-617, PSMA-R2, EB-PSMA, or PSMA I&T would be if administered to the subject.

In some embodiments, the theranostic agent remains bound to prostate cancer cells within the subject to which it is administered for a longer period of time than PSMA-11, PSMA-617, PSMA-R2, EB-PSMA, or PSMA I&T would be if administered to the subject.

In some embodiments, the theranostic agent has greater bioavailability within the subject to which it is administered than PSMA-11, PSMA-617, PSMA-R2, EB-PSMA, or PSMA I&T would have if administered to the subject.

In some embodiments, the theranostic agent is excreted hepatically from the subject to which it is administered to a greater extent (and eliminated renally to a lesser extent) than PSMA-11, PSMA-617, PSMA-R2, EB-PSMA, or PSMA I&T would be if administered to the subject.

In some embodiments, the theranostic agent binds to the salivary gland tissue of the subject to which it is administered to a lesser extent than PSMA-11, PSMA-617, PSMA-R2, EB-PSMA, or PSMA I&T would bind if administered to the subject.

In some embodiments, the theranostic agent binds to the kidney tissue of the subject to which it is administered to a lesser extent than PSMA-11, PSMA-617, PSMA-R2, EB-PSMA or PSMA I&T would bind if administered to the subject.

In a fourth aspect, this disclosure encompasses a method for inhibiting the proliferation and/or growth of malignant cells associated with increased PSMA expression. The method includes the step of contacting one or more malignant cells with an effective amount of the theranostic agent as described above, where the theranostic agent includes a metal atom chelated to the chelating moiety, and where the metal atom is an alpha, beta, or Auger emitting metal isotope. As a result of performing this step, growth and/or proliferation of the malignant cells is inhibited.

In some embodiments, the metal isotope is Lu-177, Y-90, Ho-166, Re-186, Re-188, Cu-67, Au-199, Rh-105, Ra-223, Ac-225, As-211, Pb-212, Sc-47, Sm-153, Tb-161, Tb-149, Bi-213, Bi-212, or Th-227.

In some embodiments, the malignant cells are malignant prostate or malignant breast cells. In some embodiments, the malignant cells are malignant prostate cells.

In some embodiments, the theranostic agent is contacted with the one or more malignant prostate cells in the absence of an albumen binder.

In some embodiments, the method is performed in vivo, ex vivo, or in vitro.

In a fifth aspect, this disclosure provides a method for detecting or imaging one or more cancer cells associated with increased PSMA expression in a biological sample. The method includes the steps of (a) contacting the biological sample with a theranostic agent as described above, where the theranostic agent includes a metal atom chelated to the chelating moiety, and where the metal atom is a positron or single photon emitting metal isotope, whereby the theranostic agent is differentially bound to the cancer cells within the biological sample; and (b) identifying individual cells or regions within the biological sample that are emitting signals characteristic of the metal isotope. As a result of performing these steps, the one or more cancer cells are detected or imaged.

In some embodiments, the one or more cancer cells are prostate cancer cells or breast cancer cells. In some such embodiments, the cancer cells are prostate cancer cells.

In some embodiments, the metal isotope is Ga-66, Cu-64, Y-86, Co-55, Zr-89, Sr-83, Mn-52, As-72, Sc-44, Sc-43, Ti-45, Tb-152, La-132, La-133, Ce-134, Ga-67, In-111, or Sm-153, Lu-177 or Tc-99m.

In some embodiments, the theranostic agent is contacted with the biological sample in the absence of an albumin binder.

In some embodiments, the step of identifying individual cells or regions within the biological sample that are emitting signals characteristic of the metal isotope is performed by positron emission tomography (PET) imaging, single-photon emission computed tomography (SPECT) imaging, or gamma camera planar imaging.

In some embodiments, the biological sample is part or all of a subject. In some such embodiments, the subject is a human.

In some embodiments, the theranostic agent is retained within the subject for a longer period of time than PSMA-11, PSMA-617, PSMA-R2, EB-PSMA, or PSMA I&T would be if contacted with the biological sample.

In some embodiments, the theranostic agent remains bound to prostate cancer cells within the subject for a longer period of time than PSMA-11, PSMA-617, PSMA-R2, EB-PSMA, or PSMA I&T would be bound if contacted with the biological sample.

In some embodiments, the theranostic agent has greater bioavailability within the subject than PSMA-11, PSMA-617, PSMA-R2, EB-PSMA, or PSMA I&T would have if contacted with the biological sample. In some embodiments, the theranostic agent is excreted hepatically from the subject to a greater extent (and eliminated renally to a lesser extent) than PSMA-11, PSMA-617, PSMA-R2, EB-PSMA, or PSMA I&T would be if contacted with the biological sample.

In some embodiments, the theranostic agent binds to the salivary gland tissue of the subject to a lesser extent than PSMA-11, PSMA-617, PSMA-R2, EB-PSMA, or PSMA I&T would bind if contacted with the biological sample.

In some embodiments, the theranostic agent binds to the kidney tissue of the subject to a lesser extent than PSMA-11, PSMA-617, PSMA-R2, EB PSMA, or PSMA I&T would bind if contacted with the biological sample.

In some embodiments, the biological sample is obtained from a subject. In some such embodiments, the subject is a human.

In a sixth aspect, this disclosure encompasses a method of diagnosing a cancer associated with increased PSMA expression in a subject. The method includes the steps outlined above, where the biological sample is obtained from, part of, or all of a subject. If cancer cells are detected or imaged, the subject is diagnosed with cancer.

In some embodiments, the cancer is prostate cancer or breast cancer. In some such embodiments, the cancer is prostate cancer.

In a seventh aspect, this disclosure encompasses a method of monitoring the efficacy of a cancer therapy in a human subject, where the cancer is associated with increased PSMA expression. The method includes the step of performing the detection/imaging step outlined above at two or more different times on the biological sample, where the biological sample is obtained from, part of, or all of the subject. A change in strength of the signals characteristic of the metal isotope between the two or more different times is correlated with the efficacy of the cancer therapy.

In some embodiments, the cancer is prostate cancer or breast cancer. In some such embodiments, the cancer is prostate cancer.

In some embodiments, the cancer therapy being monitored is chemotherapy and/or radiotherapy.

In an eighth aspect, this disclosure provides a method of treating a cancer associated with increased PSMA expression in a subject that includes the steps outlined above, where the biological sample is part of or all of the subject, and then subsequently directing an external radiotherapy beam to the identified individual cells or regions within the subject.

In some embodiments, the cancer is prostate cancer or breast cancer. In some such embodiments, the cancer is prostate cancer.

In a ninth aspect, this disclosure encompasses a method of determining the therapeutic dose of a theranostic agent for treating a cancer in a subject that is associated with increased PSMA expression. The method includes the steps of (a) administering to the subject a detection-facilitating dose of the theranostic agent as described above, where the theranostic agent used in the detection-facilitating dose includes a metal atom chelated to the chelating moiety, and where the metal atom is a positron or single photon emitting metal isotope; (b) subsequently detecting signals originating from the one or more prostate cancer cells within the subject that are characteristic of the metal isotope of the theranostic agent used in the detection-facilitating dose; and (c) determining from the strength of the signals detected in step (b) the therapeutic dose of the theranostic agent.

In some embodiments, the cancer is prostate cancer or breast cancer. In some such embodiments, the cancer is prostate cancer.

In some embodiments, the metal isotope of the theranostic agent used in the detection-facilitating dose is Ga-66, Cu-64, Y-86, Co-55, Zr-89, Sr-83, Mn-52, As-72, Sc-44, Sc-43, Ti-45, Tb-152, La-132, La-133, Ce-134, Ga-67, In-111, or Sm-153, Lu-177 or Tc-99m.

In some embodiments, the step of detecting signals originating from the one or more prostate cancer cells within the subject that are characteristic of the metal isotope of the theranostic agent used in the detection-facilitating dose is performed by positron emission tomography (PET) imaging, single-photon emission computed tomography (SPECT) imaging, or gamma camera planar imaging.

In some embodiments, the method further includes the step of administering to the subject the determined therapeutic dose of the theranostic agent, where the theranostic agent used in the therapeutic dose includes a metal atom chelated to the chelating moiety, and where the metal atom is an alpha, beta, or Auger emitting metal isotope.

In some embodiments, the metal isotope of the theranostic agent used in the therapeutic dose is Lu-177, Y-90, Ho-166, Re-186, Re-188, Cu-67, Au-199, Rh-105, Ra-223, Ac-225, As-211, Pb-212, Sc-47, Sm-153, Tb-161, Tb-149, Bi-213, Bi-212, or Th-227.

In a tenth aspect, this disclosure encompasses a method of treating a cancer in a subject associated with increased PSMA expression that includes the steps of (a) administering to the subject a detection-facilitating dose of the theranostic agent as described above, where the theranostic agent used in the detection-facilitating dose includes a metal atom chelated to the chelating moiety, and where the metal atom is a positron or single photon emitting metal isotope; (b) subsequently detecting signals originating from the one or more cancer cells within the subject that are characteristic of the metal isotope of the theranostic agent used in the detection-facilitating dose; (c) determining from the strength of the signals detected in step (b) the therapeutic dose of the theranostic agent; and (d) administering to the subject the determined therapeutic dose of the theranostic agent as described above, where the theranostic agent used in the therapeutic dose includes a metal atom chelated to the chelating moiety, and where the metal atom is an alpha, beta, or Auger emitting metal isotope. As a result of performing these steps, the cancer is treated in the subject.

In some embodiments, the cancer is prostate cancer or breast cancer. In some such embodiments, the cancer is prostate cancer.

In some embodiments, the metal isotope of the theranostic agent used in the detection-facilitating dose is Ga-66, Cu-64, Y-86, Co-55, Zr-89, Sr-83, Mn-52, As-72, Sc-44, Sc-43, Ti-45, Tb-152, La-132, La-133, Ce-134, Ga-67, In-111, or Sm-153, Lu-177 or Tc-99m.

In some embodiments, the step of detecting signals originating from the one or more cancer cells within the subject that are characteristic of the metal isotope of the theranostic agent used in the detection-facilitating dose is performed by positron emission tomography (PET) imaging, single-photon emission computed tomography (SPECT) imaging, or gamma camera planar imaging.

In some embodiments, the metal isotope of the theranostic agent used in the therapeutic dose is Lu-177, Y-90, Ho-166, Re-186, Re-188, Cu-67, Au-199, Rh-105, Ra-223, Ac-225, As-211, Pb-212, Sc-47, Sm-153, Tb-161, Tb-149, Bi-213, Bi-212, or Th-227.

In an eleventh aspect, this disclosure provides one or more of the theranostic agents described above for use in imaging a cancer associated with increased PSMA expression or malignant cells associated with increased PSMA expression.

In some embodiments, the cancer or cancer cells are prostate cancer or breast cancer. In some embodiments, the cancer or cancer cells are prostate cancer.

In a twelfth aspect, this disclosure provides one or more of the theranostic agents described above for use in treating a cancer associated with increased PSMA expression.

In some embodiments, the cancer is prostate cancer or breast cancer. In some such embodiments, the cancer is prostate cancer.

In a thirteenth aspect, this disclosure provides one or more of the theranostic agents described above for use in treating a cancer associated with increased PSMA expression or for use in manufacturing a medicament for treating or imaging a cancer associated with increased PSMA expression.

In some embodiments, the cancer is prostate cancer or breast cancer. In some such embodiments, the cancer is prostate cancer.

Other objects, features, and advantages of the present invention will become apparent after review of the specification, claims, and drawings.

BRIEF DESCRIPTION OF THE DRAWINGS

FIG. 4A-4C show relative distribution of $^{86}$Y-PSMA-617 (4A), $^{86}$Y-PSMA-C12 (4B), or $^{86}$Y-PSMA-PhC18 (4C) in PC3-PIP tumor xenografts. T: tumor; H: heart; L: liver; K: kidney; B: bladder.

FIG. 7A-7C show PET/CT imaging in nude mice bearing LNCap tumor xenografts with lower PSMA expression, injected intravenously with $^{86}$Y-PSMA-617 (7A), $^{86}$Y-PSMA-C12 (7B), or $^{86}$Y-PSMA-PhC18 (7C) and scanned up to 72 h post injection.

DETAILED DESCRIPTION

I. In General

Figure 1:
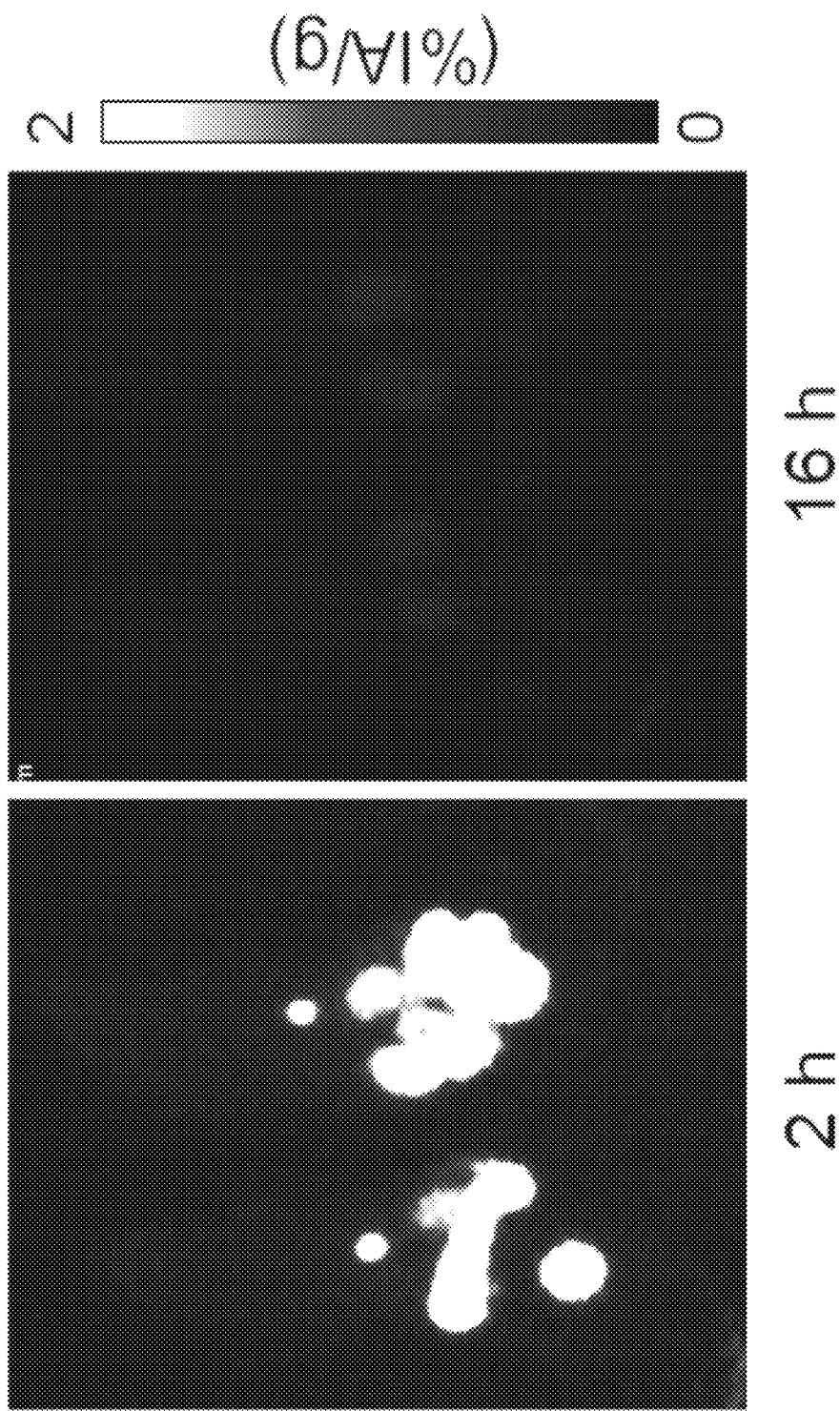
FIG. 1 shows a time course PET image of an ICR mouse following injection of $^{86}$Y-PMSA-C12.

This disclosure is not limited to the particular methodology, protocols, materials, and reagents described, as these may vary. The terminology used herein is for the purpose of describing particular embodiments only, and is not intended to limit the scope of the present invention.

As used herein and in the appended claims, the singular forms "a," "an," and "the" include plural referents unless the context clearly dictates otherwise. As well, the terms "a" (or "an"), "one or more," and "at least one" can be used interchangeably. The terms "comprising" and variations thereof do not have a limiting meaning where these terms appear in the description and claims. Accordingly, the terms "comprising," "including," and "having" can be used interchangeably.

Unless defined otherwise, all technical and scientific terms used herein have the same meanings as commonly understood by one of ordinary skill in the art to which this invention belongs. All publications and patents specifically mentioned herein are incorporated by reference for all purposes including describing and disclosing the chemicals, instruments, statistical analyses, and methodologies which are reported in the publications which might be used in connection with the invention. All references cited in this specification are to be taken as indicative of the level of skill in the art.

This disclosure is inclusive of the theranostic agents described herein (including intermediates) in any of their pharmaceutically acceptable forms, including isomers (e.g., diastereomers and enantiomers), tautomers, salts (including their anionic and cationic components), solvates, polymorphs, prodrugs, and the like. In particular, if a theranostic agent is optically active, the invention specifically includes each of the theranostic agent's enantiomers as well as racemic mixtures of the enantiomers. The terms "compound" or "theranostic agent" includes any or all of such forms, whether explicitly stated or not (although at times, "salts," "complexes" or "anions" thereof are explicitly stated).

"Pharmaceutically acceptable" as used herein means that the theranostic agent or composition or carrier is suitable for administration to a subject to achieve the treatments described herein, without unduly deleterious side effects in light of the necessity of the treatment.

The term "effective amount," as used herein, refers to the amount of the theranostic agent or dosages that will elicit the biological or medical response of a subject, tissue or cell that is being sought by the researcher, veterinarian, medical doctor, or other clinician.

As used herein, "pharmaceutically-acceptable carrier" includes any and all dry powder, solvents, dispersion media, coatings, antibacterial and antifungal agents, isotonic agents, absorption delaying agents, and the like. Pharmaceutically-acceptable carriers are materials useful for the purpose of administering the compounds in the method of the present invention, which are preferably non-toxic, and may be solid, liquid, or gaseous materials, which are otherwise inert and pharmaceutically acceptable, and are compatible with the compounds of the present invention. Examples of such carriers include, without limitation, mannitol, oils such as corn oil, buffers such as PBS, saline, polyethylene glycol, glycerin, polypropylene glycol, dimethylsulfoxide, amides such as dimethylacetamide, proteins such as albumin, and detergents such as Tween 80, and mono- and oligopolysaccharides such as glucose, lactose, cyclodextrins, and starch.

The term "administering" or "administration," as used herein, refers to providing the theranostic agent or pharmaceutical composition of the invention to a subject suffering from or at risk of the diseases or conditions to be treated or prevented.

A route of administration in pharmacology is the path by which a drug is taken into the body. Routes of administration may be generally classified by the location at which the substance is applied. Common examples may include oral and intravenous administration. Routes can also be classified based on where the target of action is. Action may be topical (local), enteral (system-wide effect, but delivered through the gastrointestinal tract), or parenteral (systemic action, but delivered by routes other than the GI tract), via lung by inhalation.

A topical administration emphasizes local effect or delayed release, and for example, the substance can be applied directly where its action is desired. Sometimes, however, the term topical may be defined as applied to a localized area of the body or to the surface of a body part, without necessarily involving target effect of the substance, making the classification rather a variant of the classification based on application location. In an enteral administration, the desired effect is typically systemic (non-local), and the substance is given via the digestive tract. In parenteral administration, the desired effect is typically systemic, and the substance is given by routes other than the digestive tract.

Non-limiting examples for topical administrations may include epicutaneous (application onto the skin), e.g., allergy testing or typical local anesthesia, inhalational, e.g. asthma medications, enema, e.g., contrast media for imaging of the bowel, eye drops (onto the conjunctiva), e.g., antibiotics for conjunctivitis, ear drops, such as antibiotics and corticosteroids for otitis externa, and those through mucous membranes in the body.

Enteral administration may be administration that involves any part of the gastrointestinal tract and has systemic effects. The examples may include those by mouth (orally), many drugs as tablets, capsules, or drops, those by gastric feeding tube, duodenal feeding tube, or gastrostomy, many drugs and enteral nutrition, and those rectally, various drugs in suppository.

Examples of parenteral administrations may include intravenous (into a vein), e.g. many drugs, total parenteral nutrition intra-arterial (into an artery), e.g., vasodilator drugs in the treatment of vasospasm and thrombolytic drugs for treatment of embolism, intraosseous infusion (into the bone marrow), intra-muscular, intracerebral (into the brain parenchyma), intracerebroventricular (into cerebral ventricular system), intrathecal (an injection into the spinal canal), and subcutaneous (under the skin). Among them, intraosseous infusion is, in effect, an indirect intravenous access because the bone marrow drains directly into the venous system. Intraosseous infusion may be occasionally used for drugs and fluids in emergency medicine and pediatrics when intravenous access is difficult.

As used herein, the term "intraperitoneal injection" or "IP injection" refers to the injection of a substance into the peritoneum (body cavity). IP injection is more often applied to animals than to humans. In general, IP injection may be preferred when large amounts of blood replacement fluids are needed, or when low blood pressure or other problems prevent the use of a suitable blood vessel for intravenous injection.

As used herein, the term "PSMA-11" refers to the PSMA-targeting ligand known in the art that has the structure:

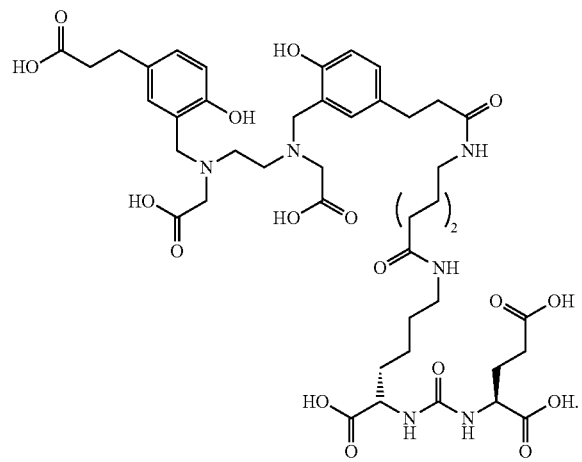

As used herein, the term "PSMA-617" refers to the PSMA-targeting ligand known in the art that has the structure:

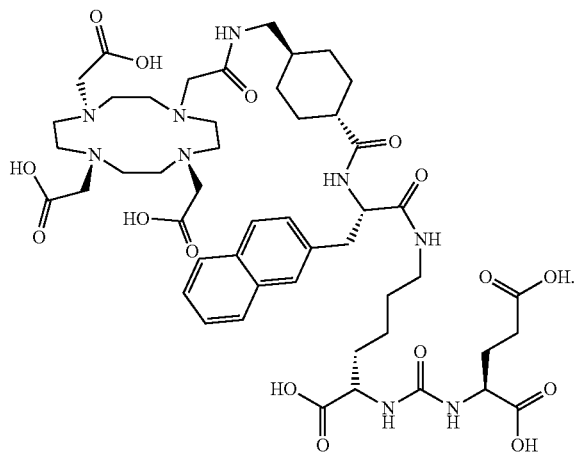

As used herein, the term "PSMA I&T" refers to the PSMA-targeting ligand known in the art that has the structure:

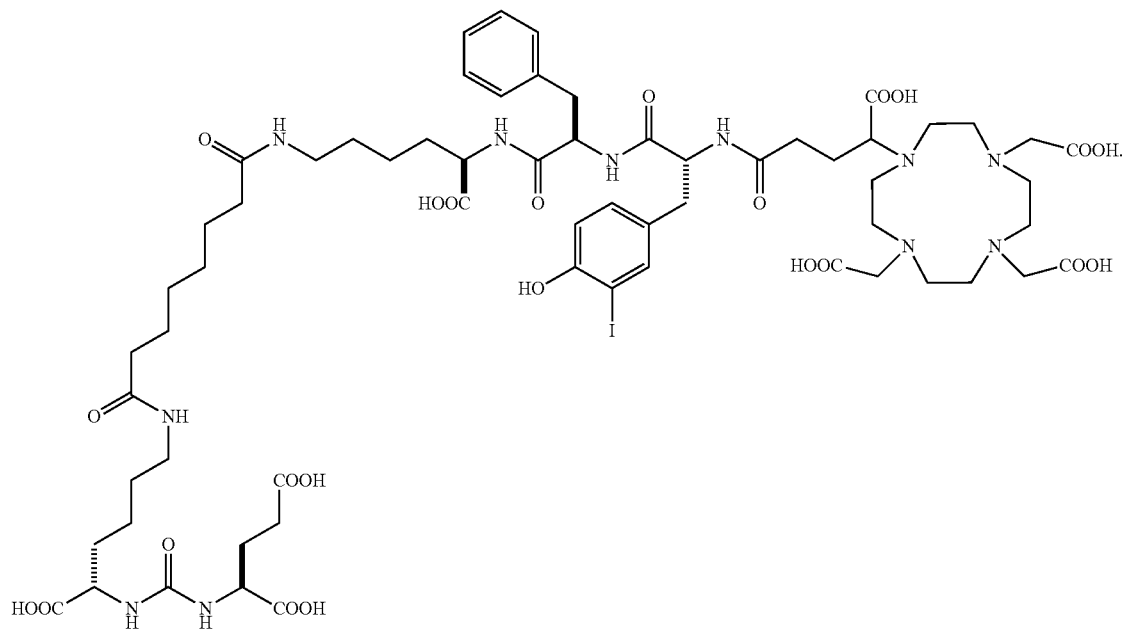

II. Theranostic Agents

In certain aspects, the disclosure is directed to PSMA-targeting theranostic agents that may optionally be labeled with a radioactive metal isotope for detection/imaging of cancer cells associated with increased PSMA expression in a subject or in a biological sample, or for the treatment of a cancer associated with increased PSMA expression in a subject. The theranostic agents include a PSMA-targeting moiety and a chelating moiety that can chelate the radioactive metal isotope. These two moieties are linked by a linker that includes an aliphatic chain. By changing the length of the aliphatic chain, we can tune and optimize the pharmacokinetics, bioavailability, circulation half-life, and other parameters of the disclosed theranostic agents.

The disclosure is not limited to a specific type of cancer, but instead encompasses compositions and methods for detecting and/or treating any type of cancer that is associated with increased PSMA expression. Non-limiting examples of such cancers include prostate cancer and breast cancer.

A. Radioactive Metal Isotopes for Cancer Treatment

For the disclosed methods of therapeutically treating a cancer associated with increased PSMA expression, any radioactive metal isotope known to emit ionizing radiation in a form that would result in the death of cancer cells (e.g., prostate cancer cells) that bind to or take up the theranostic agent can be incorporated into the theranostic agent by chelation. In some embodiments, the radioactive metal isotope emits its ionizing radiation in a form that minimizes damage to tissue outside of the cells that take up or bind to the labeled theranostic agent.

Non-limiting examples of radioactive metal isotopes that could be used include Lu-177, Y-90, Ho-166, Re-186, Re-188, Cu-67, Au-199, Rh-105, Ra-223, Ac-225, As-211, Pb-212, Sc-47, Sm-153, Tb-161, Tb-149, Bi-213, Bi-212, or Th-227.

In some embodiments, the longer retention rates of the presently disclosed theranostic compounds in cancer cells and tumors provide a synergistic advantage when combined with some of the radio isotopes contemplated for use herein that have longer half-lives. In other words, by combining therapeutic radio isotopes (e.g., those emitting ionizing radiation) that have longer half-lives with the presently disclosed targeting moieties that have longer cancer cell/tumor retention rates, the resulting theranostic agents can more effectively treat cancer by providing a prolonged therapeutically effective treatment duration compared to other treatment modalities. As a result, subjects receiving these theranostic agents can receive effective treatment with either a reduced dose of a therapeutic radio isotope and/or a reduced number of administrations of the theranostic agent.

In one particular embodiment, a theranostic agent has a long-lived isotope for cancer treatment, wherein the half-life of the isotope is at least about 6, 7, 8, 9, 10, 11, 12, 13, 14, 15, 16, 17, 18, 19 or 20 days. For example, the radio isotope can be 177Lu, which has a half-life of 6 days, or 225 Ac, which has a half-life of 10 days, or 227Th, which has a half-life of 20 days.

B. Radioactive Metal Isotopes for Malignant Solid Tumor Detection/Imaging

For the disclosed methods of detecting/imaging a cancer associated with increased PSMA expression, any radioactive metal isotope known to emit radiation in a form that is readily detectable by conventional imaging means can be incorporated into the theranostic agent by chelation. Non-limiting examples of "conventional imaging means" include gamma ray detection, PET scanning, and SPECT scanning. Non-limiting examples of radioactive metal isotopes that could be used include Ga-66, Cu-64, Y-86, Co-55, Zr-89, Sr-83, Mn-52, As-72, Sc-44, Sc-43, Ti-45, Tb-152, La-132, La-133, Ce-134, Ga-67, In-111, or Sm-153, Lu-177 or Tc-99m.

PSMA-targeting moieties, such as those disclosed by Machulkin et al. (E. Machulkin, Yan A. Ivanenkov, Anastasia V. Aladinskaya, Mark S. Veselov, Vladimir A. Aladinskiy, Elena K. Beloglazkina, Victor E. Koteliansky, Artem G. Shakhbazyan, Yuri B. Sandulenko & Alexander G. Majouga (2016) Small-molecule PSMA ligands. Current state, SAR and perspectives, Journal of Drug Targeting, 24:8, 679-693, DOI: 10.3109/1061186X.2016.1154564), which is incorporated by reference herein.

D. Non-limiting Exemplary Theranostic Agents

The disclosed structures utilize a backbone that includes a chelating moiety linked with an aliphatic hydrocarbon chain to a PSMA-targeting moiety. Once synthesized, the theranostic agents must harbor formulation properties that render them suitable for injection while retaining prostate tumor selectivity. A non-limiting exemplary series of two different theranostic agents, PSMA-C12 and PSMA-PhC18, follows. On the left side of two structures is the chelating moiety to which the radioactive metal isotope is chelated to produce the final imaging or therapeutic agent. The aliphatic linker is in the center of each structure, and the PSMA-targeting moiety is on the right side of each structure.

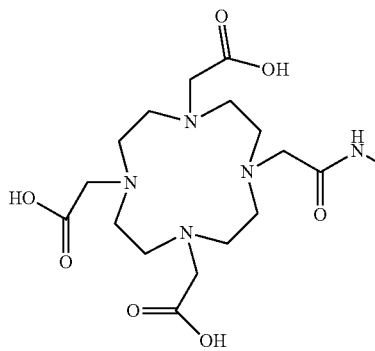
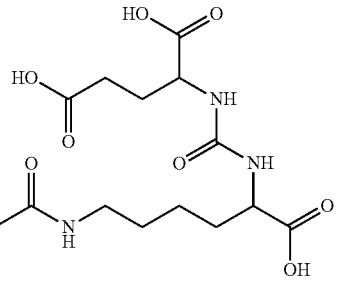

PSMA-C12

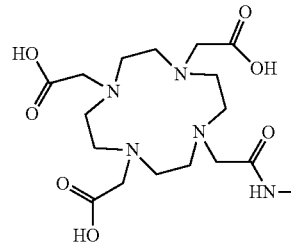

PSMA-PhC18

In one embodiment, another claim could be the more sensitive detection of primary prostate disease since the urinary bladder would not obscure the lesion given that the agent is not excreted renally.

C. PSMA-Targeting Moieties

The disclosed compositions and methods may use any moiety that effectively targets PSMA. Non-limiting examples of PSMA-targeting moieties that may be used include thiol-based, urea-based, and phosphorous-based E. Methods of Synthesizing Exemplary Theranostic Agents.

Synthesis of PSMA-targeting lysine-ureido-glutamate ligand 2 is shown in Scheme 1. Synthesis was started from di-tert-butyl ester of L-glutamic acid via the formation of intermediate isocyanate by reaction with triphosgene, followed by the reaction with $N^\varepsilon$—Z-L-lysine t-butyl ester to provide compound 1 according to the published procedure (Ivanenkov I A et al., Bioorg Med Chem Lett, 2019, 29, 1246-1255). Removal of Cbz group in 1 by hydrogenation gave the core ligand 2.

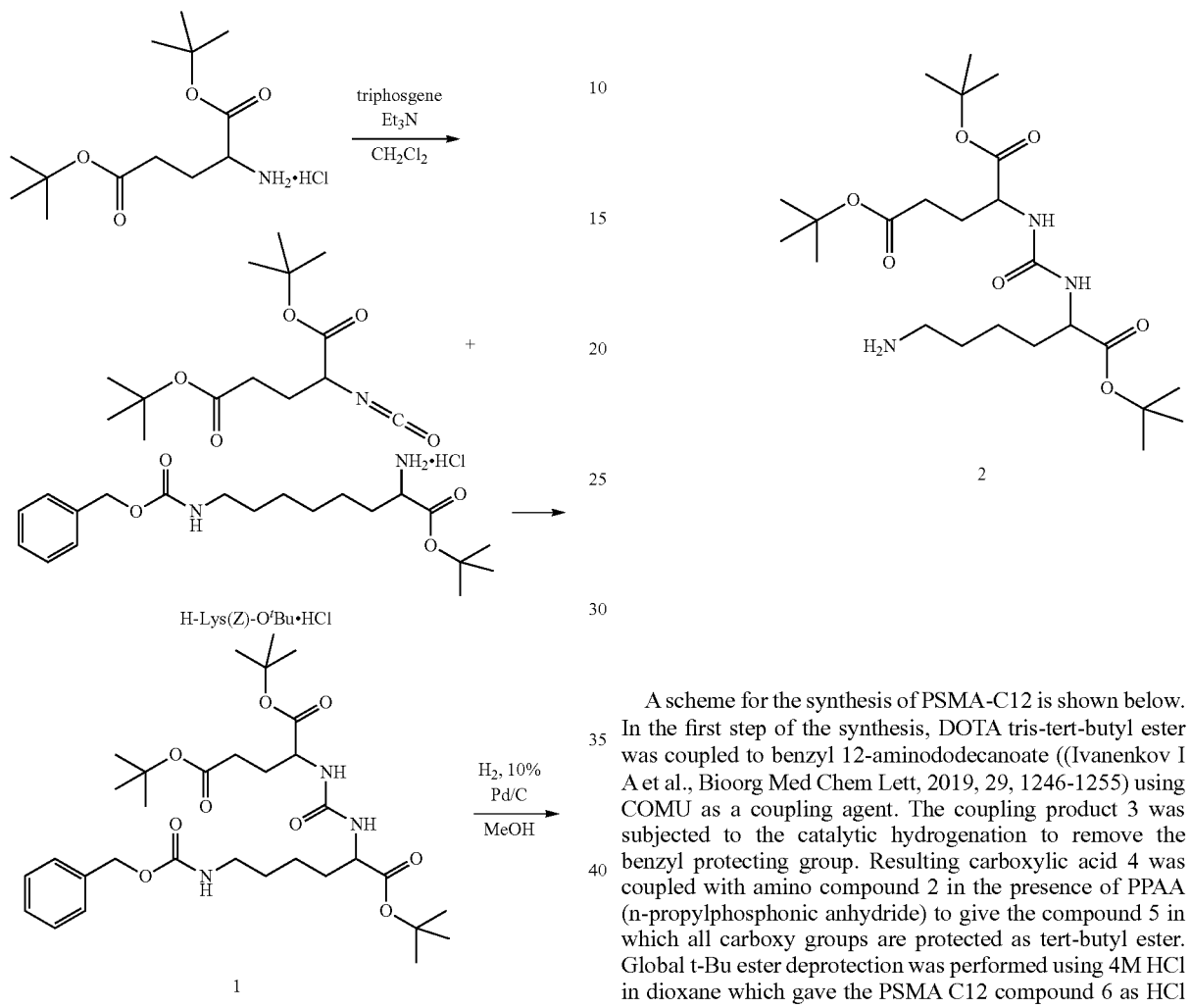

A scheme for the synthesis of PSMA-C12 is shown below. In the first step of the synthesis, DOTA tris-tert-butyl ester was coupled to benzyl 12-aminododecanoate ((Ivanenkov I A et al., Bioorg Med Chem Lett, 2019, 29, 1246-1255) using COMU as a coupling agent. The coupling product 3 was subjected to the catalytic hydrogenation to remove the benzyl protecting group. Resulting carboxylic acid 4 was coupled with amino compound 2 in the presence of PPAA (n-propylphosphonic anhydride) to give the compound 5 in which all carboxy groups are protected as tert-butyl ester. Global t-Bu ester deprotection was performed using 4M HCl in dioxane which gave the PSMA C12 compound 6 as HCl salt.

Scheme 2

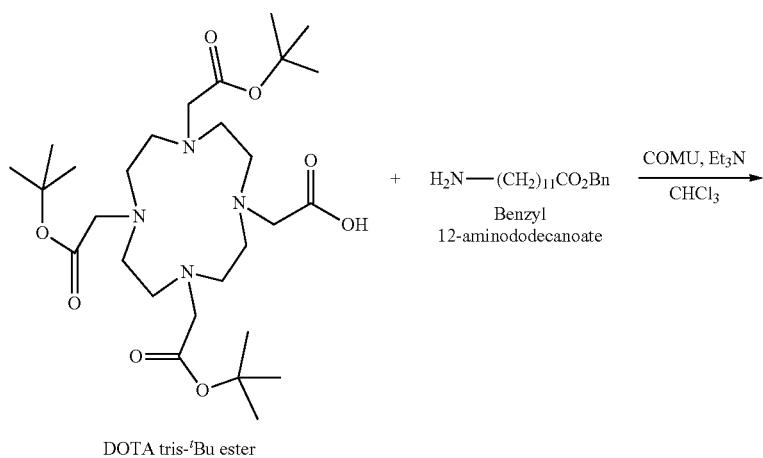

-continued
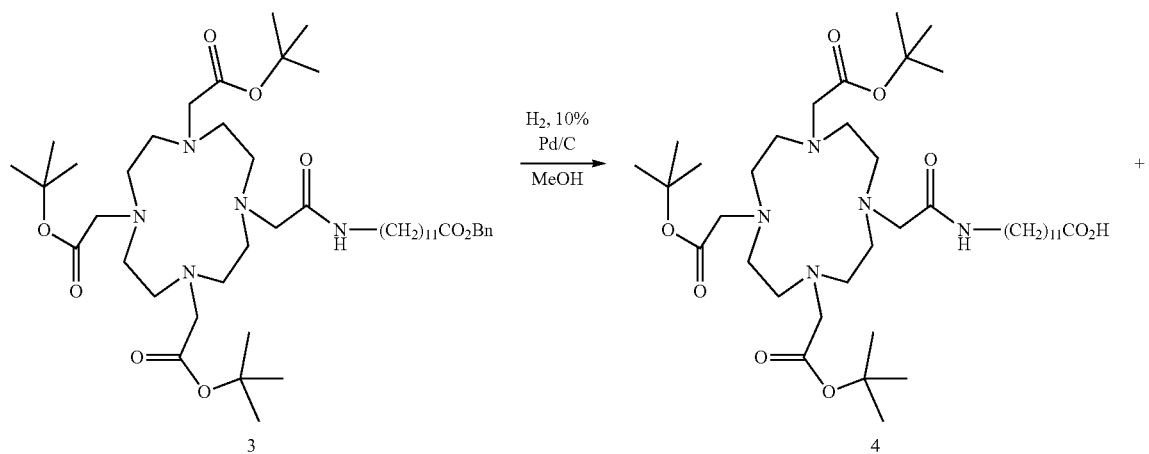
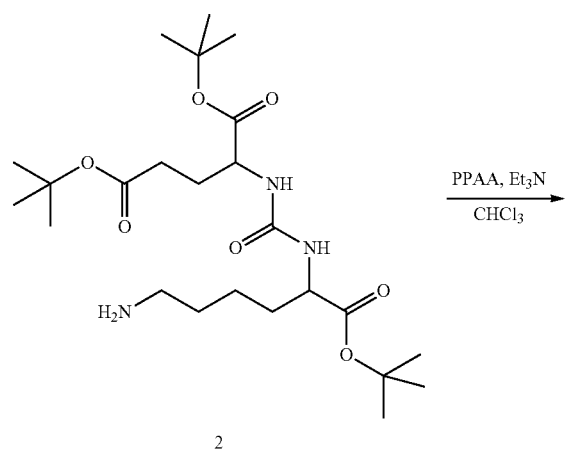
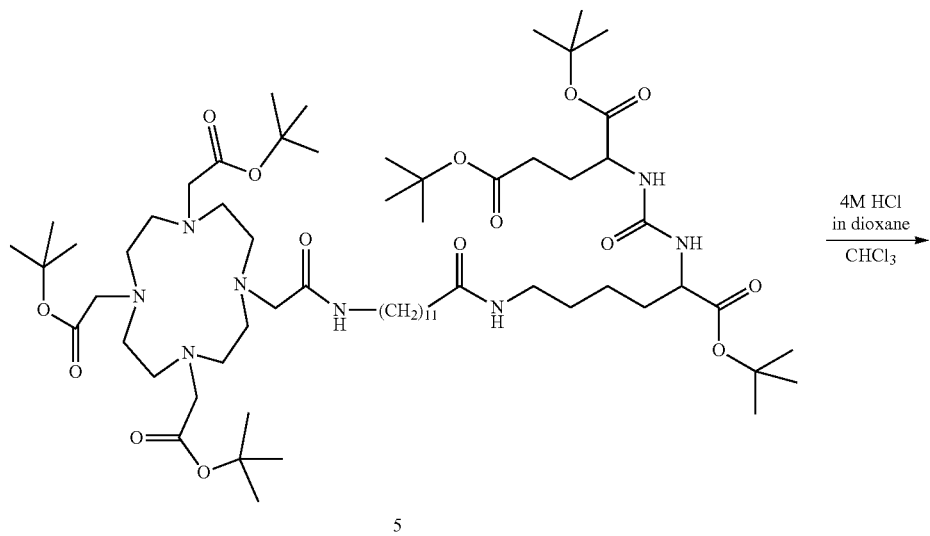

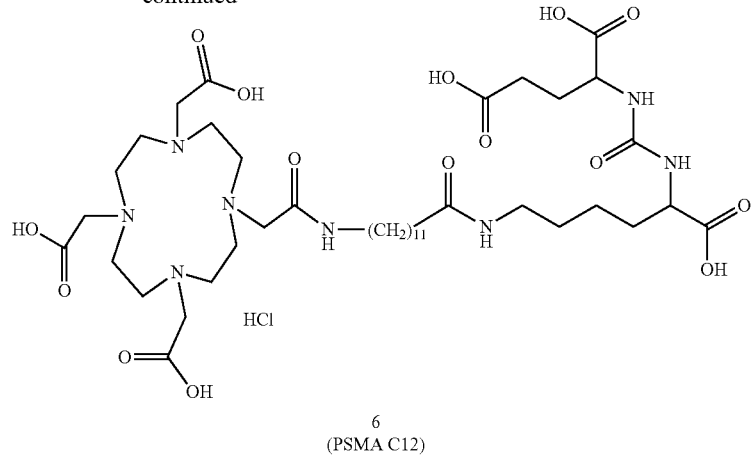

6
(PSMA C12)

Synthesis of PSMA PhC18 compound is shown in Scheme 3. Reaction of the core ligand 2 with 18-(p-iodophenyl)-octadecanoic acid mediated by PPAA resulted in compound 7. Aromatic iodide in 7 was substituted by azide by CuI/N,N'-dimethylethylenediamine-catalyzed reaction (Andersen J et al., Synlett, 2005, 2209-2213). Reduction of the aromatic azide in 8 by the catalytic hydrogenation gave the aromatic amine 9. This compound was coupled with DOTA tris-tert-butyl ester to provide the fully protected PSMA PhC18 precursor 10. All t-Bu ester groups were removed with 4M HCl in dioxane to give the PSMA PhC18 compound 11 as HCl salt.

Scheme 3

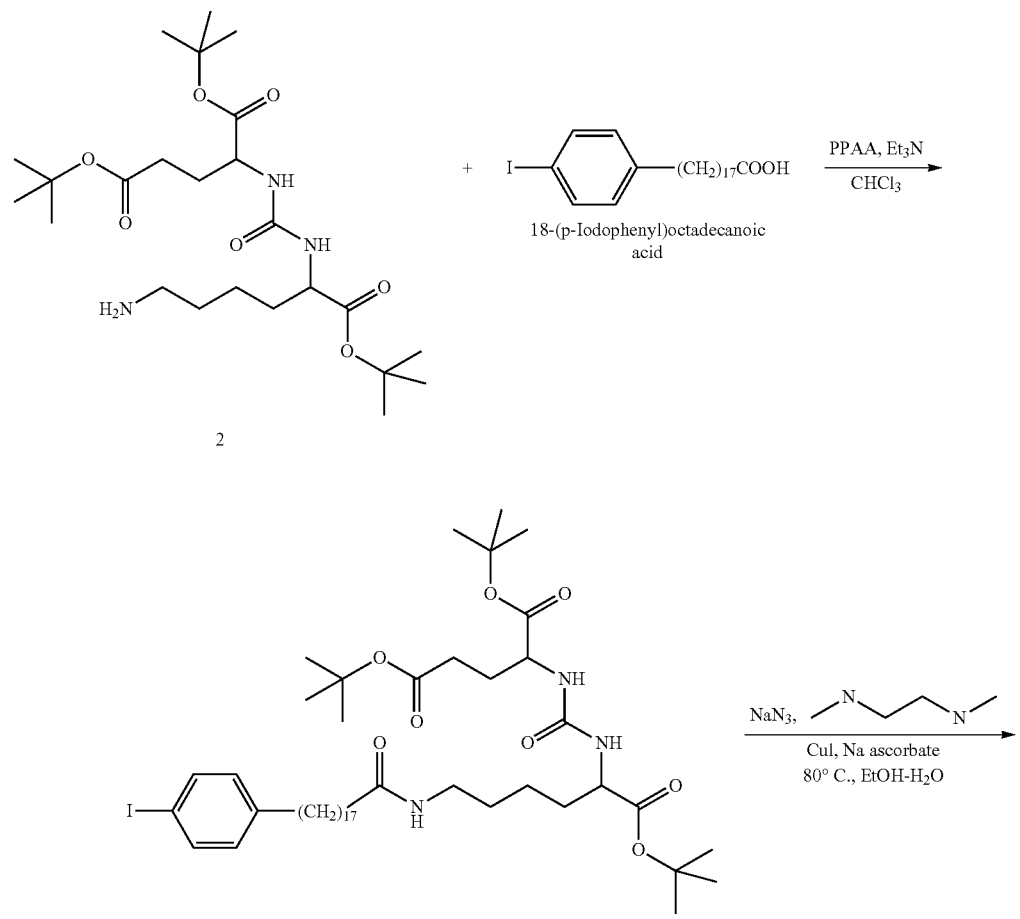

-continued
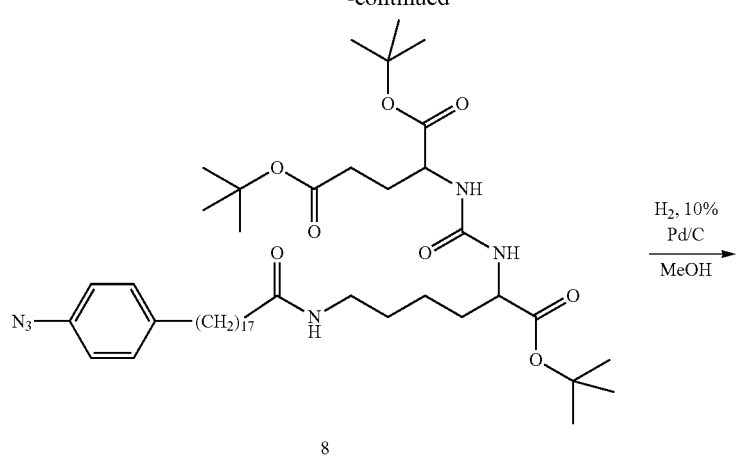
8
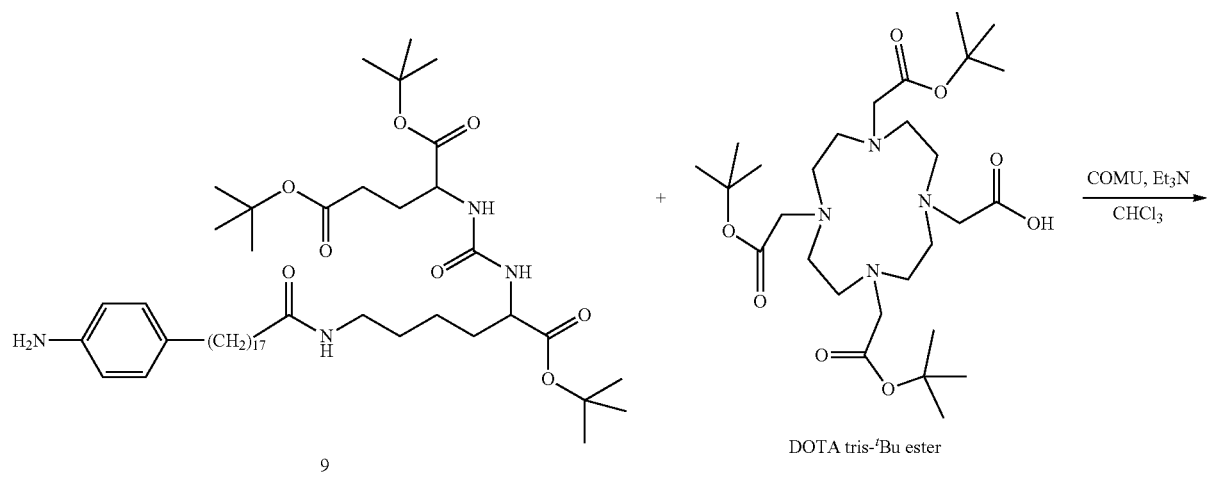
9        DOTA tris-$^t$Bu ester
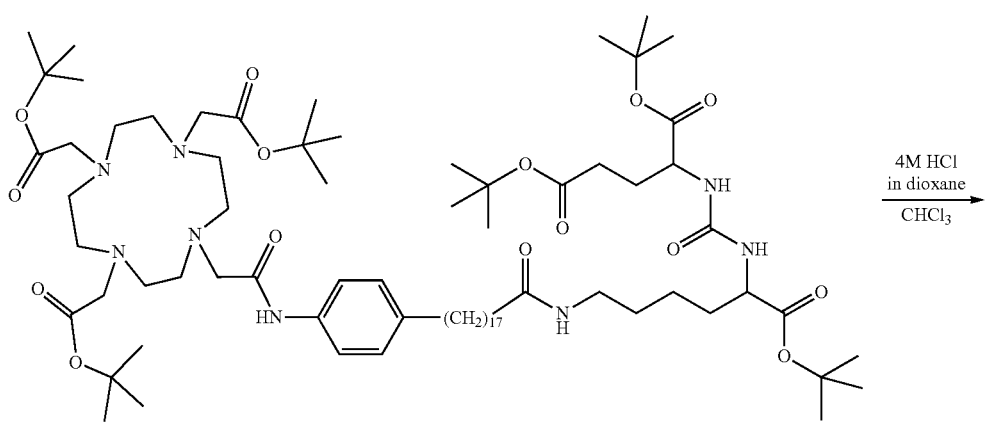
10

-continued

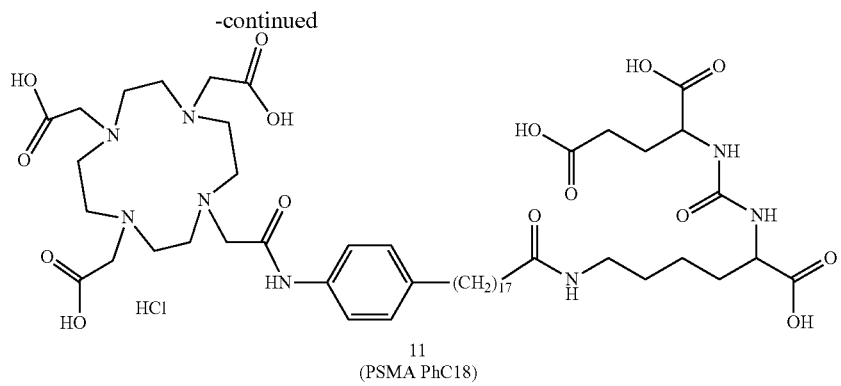

11
(PSMA PhC18)

F. Charge Balance of Theranostic Agents

As noted throughout this disclosure, a number of different known chelating moieties may be used in the disclosed theranostic agents. In preferred embodiments where a metal radioisotope is chelated to the chelating moiety, the resulting complex as a whole is electrically neutral. Typically, the selected metal radioisotope is in the form of a positively charged cation, and thus the chelating moiety is selected to have a negative charge that is equal in magnitude to the positive charge of the metal cation.

G. Adjusting the Length of the Aliphatic Hydrocarbon Linker to Tune Desired Properties The aliphatic hydrocarbon chain used as a linker in the disclosed theranostic agents is the key to tuning and optimizing the properties of the theranostic agents. The linker can be from 12 to 21 carbons in length, and it has been found that by shortening and/or lengthening the carbon chain, a number of relevant chemical and biological properties of the theranostic agents can be changed. Accordingly, the length of the linker can be selected to optimize such properties for a given specific use.

Fundamentally, changing the length of the aliphatic hydrocarbon chain affects the hydrophobicity of the theranostic agent. Specifically, as the chain is lengthened from 12 to 21 carbon atoms, the theranostic agent as a whole becomes increasingly hydrophobic. It has been found that this fundamental change is correlated with a number of relevant biological properties of the disclosed theranostic agents, giving them surprising advantages over previously known PSMA-targeting ligands, such PSMA-11, PSMA-617, PSMA-R2, EB-PSMA, or PSMA I&T.

In one example, lengthening the hydrocarbon chain was found to increase the circulation half-life of the theranostic agent within the subject to which it is administered. When the theranostic agent is retained for a longer period within the subject, a single dose can provide prostate cancer therapy and can facilitate prostate cancer detection for longer periods of time.

In a second related example, lengthening the hydrocarbon chain was found to increase the length of time for which the theranostic agent remains bound to the prostate cancer cells within the subject. Again, this extends the time for which a single dose can provide effective prostate cancer therapy and can facilitate prostate cancer detection.

In a third example, lengthening the hydrocarbon chain was found to increase the bioavailability of the theranostic agent within the subject to which it is administered. Furthermore, theranostic agents having the disclosed linkers do not need to be administered with an albumin binder, which further increases their bioavailability relative to previously known PSMA-targeting ligands. Increased bioavailability means that the effective dosage of the theranostic agents is less, which is a particular advantage when administering a radioactive (and potentially toxic) metal to a subject.

In a fourth example, lengthening the hydrocarbon chain was found to affect the excretion route of the theranostic agent. When the hydrocarbon chain is twelve carbons in length, the theranostic agent is primarily excreted renally, as has been reported for previously known PSMA-targeting ligands. However, as the hydrocarbon chain is lengthened, the theranostic agent is excreted hepatically to a greater extent (and excreted renally to a lesser extent). Accordingly, the length of the hydrocarbon chain of the theranostic agent can be selected to obtain an optimal combination of renal and/or hepatic elimination.

In a fifth example, lengthening the hydrocarbon chain was found to decrease the extent of off-target binding for the theranostic agent. Specifically, it was found that theranostic agents having longer hydrocarbon chains did not collect or bind to the salivary gland or kidney tissue of a subject to which they were administered, as has been reported for previously known PSMA-targeting ligands. Accordingly, the disclosed theranostic agents have improved prostate cancer-targeting profiles.

Finally, in alpha particle-based therapies, it is important that the alpha-emitting radioisotope be delivered as close as possible to the targeted prostate cancer cells. Because the disclosed theranostic agents lack the bulky linkers (typically including one or more phenyl groups) used in previously known PSMA-targeting ligands, the disclosed theranostic agents can be more effectively optimized for alpha particle-based therapies.

In some embodiments, it is contemplated that the presently disclosed theranostic agents will provide a more sensitive detection of primary prostate disease because the urinary bladder would not obscure the lesion given that the agent is not excreted renally. In this way, it is contemplated that a method of treating an individual suspect of having prostate cancer can include administering an effective amount of a theranostic agent disclosed herein and detecting primary prostate disease in the individual using a suitable manner of detection according to the radio isotope employed.

In some embodiments, dual function theranostic agents are contemplated where the radio isotope chelated to the agent has both utility as an imaging agent and as a anti-cancer therapeutic.

H. Dosage Forms and Administration Methods

Any route of administration may be suitable for administering the disclosed theranostic agents to a subject. In one embodiment, the disclosed theranostic agents may be administered to the subject via intravenous injection. In another embodiment, the disclosed theranostic agents may be administered to the subject via any other suitable systemic deliveries, such as parenteral, intranasal, sublingual, rectal, or transdermal administration.

In another embodiment, the disclosed theranostic agents may be administered to the subject via nasal systems or mouth through, e.g., inhalation.

In another embodiment, the disclosed theranostic agents may be administered to the subject via intraperitoneal injection or IP injection.

In certain embodiments, the disclosed theranostic agents may be provided as pharmaceutically acceptable salts. Other salts may, however, be useful in the preparation of the theranostic agents or of their pharmaceutically acceptable salts. Suitable pharmaceutically acceptable salts include, without limitation, acid addition salts which may, for example, be formed by mixing a solution of the theranostic agent with a solution of a pharmaceutically acceptable acid such as hydrochloric acid, sulphuric acid, methanesulphonic acid, fumaric acid, maleic acid, succinic acid, acetic acid, benzoic acid, oxalic acid, citric acid, tartaric acid, carbonic acid, or phosphoric acid.

Where the disclosed theranostic agents have at least one asymmetric center, they may accordingly exist as enantiomers. Where the disclosed alkylphosphocholine analogs possess two or more asymmetric centers, they may additionally exist as diastereomers. All such isomers and mixtures thereof in any proportion are encompassed within the scope of the present disclosure.

The disclosure also includes methods of using pharmaceutical compositions comprising one or more of the disclosed theranostic agents in association with a pharmaceutically acceptable carrier. Preferably these compositions are in unit dosage forms such as tablets, pills, capsules, powders, granules, sterile parenteral solutions or suspensions, metered aerosol or liquid sprays, drops, ampoules, auto-injector devices or suppositories; in unit dosage forms for parenteral, intranasal, sublingual, or rectal administration, or in unit dosage forms for administration by inhalation or insufflation.

For preparing solid compositions such as tablets, the principal active ingredient is mixed with a pharmaceutically acceptable carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture for a compound of the present invention, or a pharmaceutically acceptable salt thereof. When referring to these preformulation compositions as homogeneous, it is meant that the active ingredient is dispersed evenly throughout the composition so that the composition may be easily subdivided into equally effective unit dosage forms such as tablets, pills, and capsules. This solid pre-formulation composition is then subdivided into unit dosage forms of the type described above containing from 0.1 to about 500 mg of the active ingredient of the present invention. Typical unit dosage forms contain from 1 to 100 mg, for example, 1, 2, 5, 10, 25, 50, or 100 mg, of the active ingredient. The tablets or pills of the novel composition can be coated or otherwise compounded to provide a dosage affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the theranostic agents may be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles. Suitable dispersing or suspending agents for aqueous suspensions include synthetic and natural gums such as tragacanth, acacia, alginate, dextran, sodium caboxymethylcellulose, methylcellulose, polyvinylpyrrolidone, or gelatin.

The disclosed theranostic agents are particularly useful when formulated in the form of a pharmaceutical injectable dosage, including in combination with an injectable carrier system. As used herein, injectable and infusion dosage forms (i.e., parenteral dosage forms) include, but are not limited to, liposomal injectables or a lipid bilayer vesicle having phospholipids that encapsulate an active drug substance. Injection includes a sterile preparation intended for parenteral use.

Five distinct classes of injections exist as defined by the USP: emulsions, lipids, powders, solutions, and suspensions. Emulsion injection includes an emulsion comprising a sterile, pyrogen-free preparation intended to be administered parenterally. Lipid complex and powder for solution injection are sterile preparations intended for reconstitution to form a solution for parenteral use. Powder for suspension injection is a sterile preparation intended for reconstitution to form a suspension for parenteral use. Powder lyophilized for liposomal suspension injection is a sterile freeze dried preparation intended for reconstitution for parenteral use that is formulated in a manner allowing incorporation of liposomes, such as a lipid bilayer vesicle having phospholipids used to encapsulate an active drug substance within a lipid bilayer or in an aqueous space, whereby the formulation may be formed upon reconstitution. Powder lyophilized for solution injection is a dosage form intended for the solution prepared by lyophilization ("freeze drying"), whereby the process involves removing water from products in a frozen state at extremely low pressures, and whereby subsequent addition of liquid creates a solution that conforms in all respects to the requirements for injections. Powder lyophilized for suspension injection is a liquid preparation intended for parenteral use that contains solids suspended in a suitable fluid medium, and it conforms in all respects to the requirements for Sterile Suspensions, whereby the medicinal agents intended for the suspension are prepared by lyophilization. Solution injection involves a liquid preparation containing one or more drug substances dissolved in a suitable solvent or mixture of mutually miscible solvents that is suitable for injection.

Solution concentrate injection involves a sterile preparation for parenteral use that, upon addition of suitable solvents, yields a solution conforming in all respects to the requirements for injections. Suspension injection involves a liquid preparation (suitable for injection) containing solid particles dispersed throughout a liquid phase, whereby the particles are insoluble, and whereby an oil phase is dispersed throughout an aqueous phase or vice-versa. Suspension liposomal injection is a liquid preparation (suitable for injection) having an oil phase dispersed throughout an aqueous phase in such a manner that liposomes (a lipid bilayer vesicle usually containing phospholipids used to encapsulate an active drug substance either within a lipid bilayer or in an aqueous space) are formed. Suspension sonicated injection is a liquid preparation (suitable for injection) containing solid particles dispersed throughout a liquid phase, whereby the particles are insoluble. In addition, the product may be sonicated as a gas that is bubbled through the suspension resulting in the formation of microspheres by the solid particles.

The parenteral carrier system may include one or more pharmaceutically suitable excipients, such as solvents and co-solvents, solubilizing agents, wetting agents, suspending agents, thickening agents, emulsifying agents, chelating agents, buffers, pH adjusters, antioxidants, reducing agents, antimicrobial preservatives, bulking agents, protectants, tonicity adjusters, and special additives.

The following example is for illustrative purposes only, and does not limit the scope of the present invention in any way. Indeed, various modifications of the invention in addition to those shown and described herein will become apparent to those skilled in the art from the foregoing description and the following example and fall within the scope of the appended claims.

III. EXAMPLES

Example No. 1 In vivo Imaging Proof of Concept

Summary

In this example, we demonstrate that PSMA-C12 and PSMA PhC-18 (radiolabeled with 86Y) are taken up by and retained within ICR mice, thus providing proof of concept for using the disclosed theranostic agents as targeted radiotherapy and/or imaging agents. In addition, we found that the difference in hydrocarbon chain length between the two compounds affected properties relevant to the use of the theranostic agents, thus providing proof of concept for changing the length of the hydrocarbon chain in order to tune and/or optimize the disclosed theranostic agents for a specific use, as outlined above.

Materials, Methods, and Results

See above for the structures of the PSMA-C12 and PSMA-PhC18 compounds. Hydrophobicity was changed by changing the number of members in the aliphatic portion of the molecule.

Compounds PSMA-C12 and PSMA-PhC18 were dissolved in water at a concentration of 1-2 mg/mL. Radiolabeling with Y-86 was carried out in NaOAc buffer (pH 5.0) at 90-95 C for 30 min to 1 h at constant stirring. Ten micrograms of compound per mCi of 86Y were employed, affording quantitative radiochemical yields. Purification of the compounds was carried out using reverse-phase solid-phase chromatography and purified compounds were redissolved in physiological injection media (e.g., normal saline). Quality control was conducted using reverse-phase HPLC.

Figure 2:
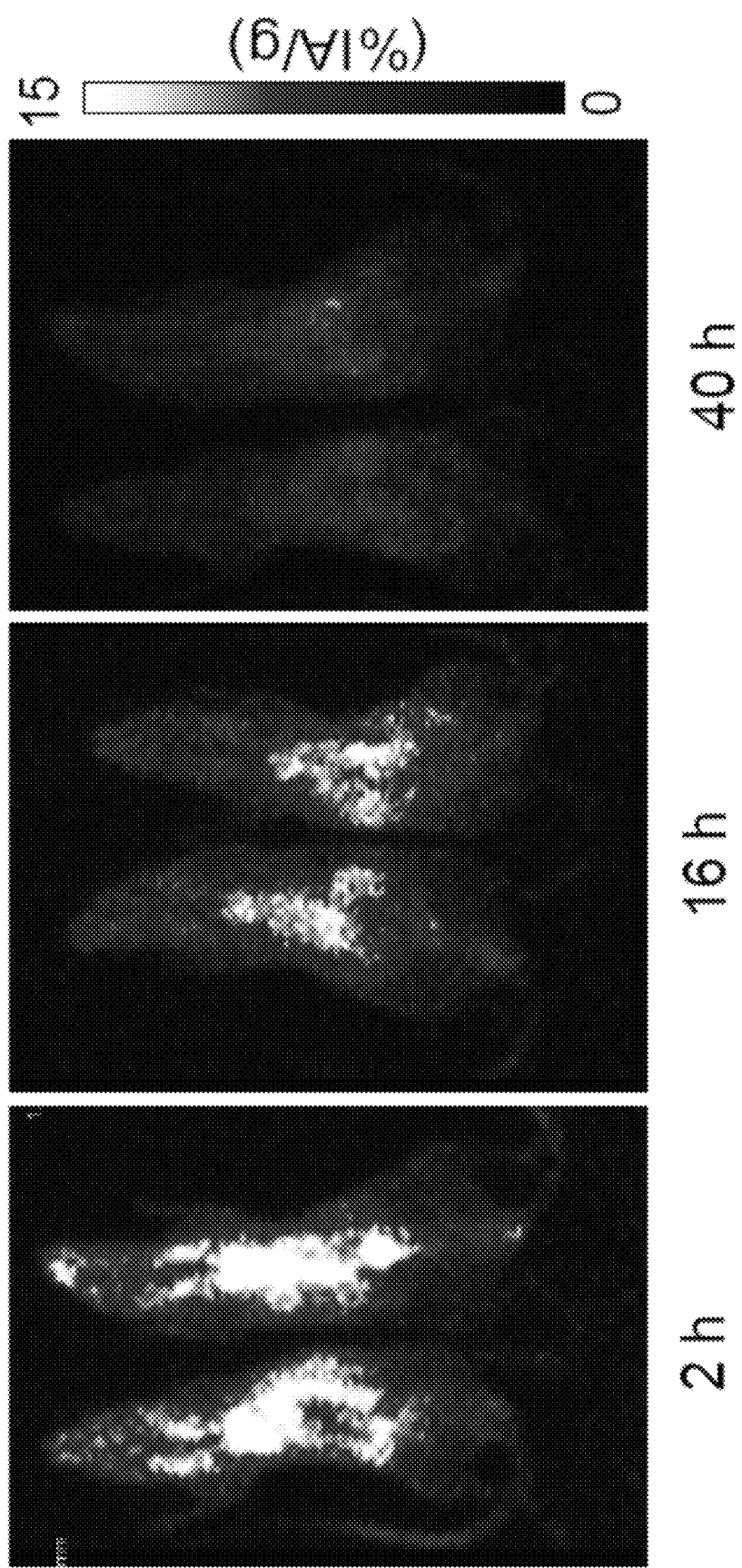
FIG. 2 shows a time course PET image of an ICR mouse following injection of $^{86}$Y-PMSA-PhC18.

In PET/CT imaging studies, 100-250 µCi of $^{86}$Y-PSMA-C12 and $^{86}$Y-PSMA-PhC18 were intravenously administered into normal ICR mice, and mice were scanned on days 0, 1, and 2 after injection. The results are shown in FIG. 1 (for $^{86}$Y-PSMA-C12) and in FIG. 2 (for $^{86}$Y-PSMA-PhC18). Blood circulation kinetics were analyzed through a region of interest analysis of the heart.

PET imaging revealed markedly different blood kinetics and excretion profiles between the two compounds. Whereas $^{86}$Y-PSMA-C12 behaved like the "classical" PSMA inhibitors—having short circulation half-life and renal excretion, $^{86}$Y-PSMA-PhC18 showed prolonged circulation and hepatobiliary excretion. To our knowledge, $^{86}$Y-PSMA-PhC18 is the only PSMA inhibitor showing long circulation without albumin binding, and that has predominantly hepatic excretion. These features have clear advantages over other previously known PSMA ligands for prostate cancer theranostics.

Example No. 2 Theranostic Agent Comparison Studies

In this example, we compared characteristics of PSMA-617, PSMA-C12, and PSMA PhC-18 theranostic compounds.

Materials, Methods, and Results

See above for the structures of the PSMA-C12 and PSMA-PhC18 compounds.

Compounds PSMA-617, PSMA-C12, and PSMA-PhC18 were radiolabeled with Lu-177 or $^{86}$Y as described above. Quality control was conducted using reverse-phase HPLC.

Table 1 shows partition (log P) and distribution (log D) coefficients for $^{177}$Lu-PSMA-617, $^{177}$Lu-PSMA-C12, and $^{177}$Lu-PSMA-PhC18. $^{177}$Lu-PSMA-617 and $^{177}$Lu-PSMA-C12 have similar hydrophobicity while $^{177}$Lu-PSMA-PhC18 is two orders of magnitude more hydrophobic.

TABLE 1

Hydrophobicity Comparison

| Compound | LogD | LogP |
| --- | --- | --- |
| $^{177}$Lu-PSMA-617 | −3.2 | −2.8 |
| $^{177}$Tu-PSMA-C12 | −2.9 | −2.6 |
| $^{177}$Lu-PSMA-PhC18 | −1.2 | −0.8 |

Figure 3:
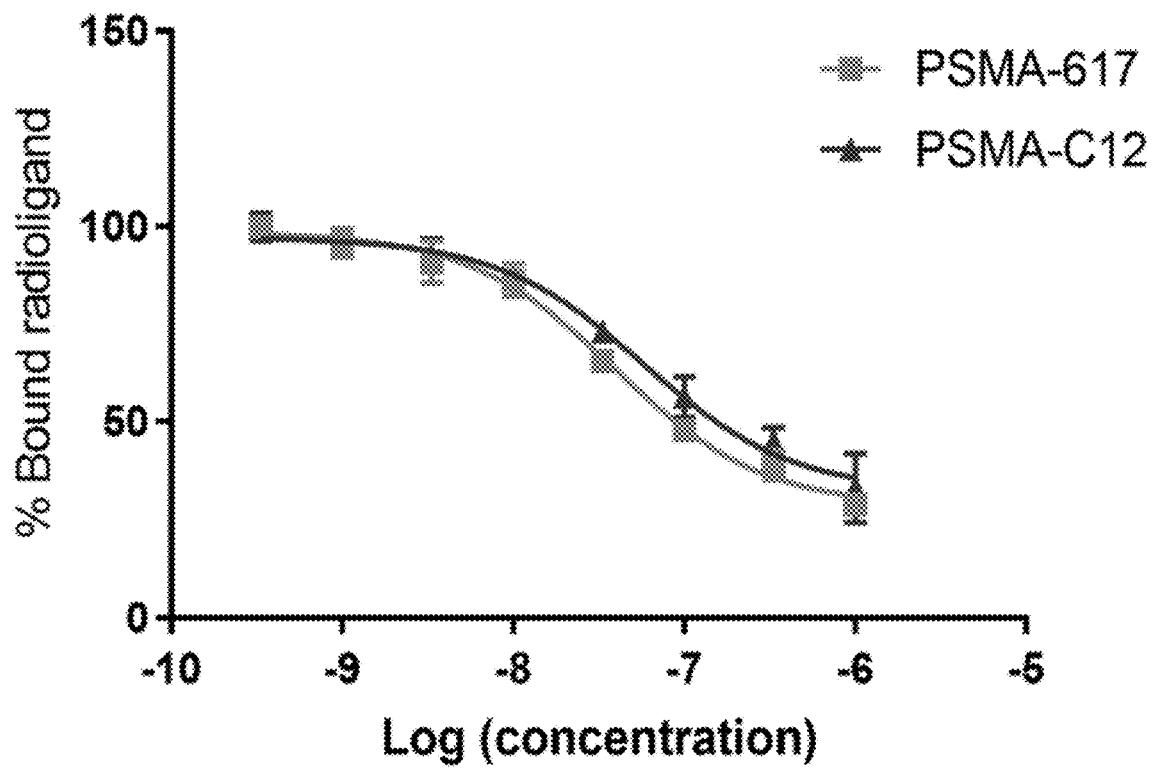
FIG. 3 shows competitive binding assay for PSMA-617 and PSMA-C12 in LNCap cells using $^{86}$Y as a radioligand.

Competitive binding assays were performed in LNCap cells (PSMA positive, androgen-sensitive human prostate adenocarcinoma cells) using 86Y as a radioligand. As shown in FIG. 3, $^{86}$Y-PSMA-617 and $^{86}$Y-PSMA-C12 displayed similar binding affinities for PSMA expressing cells with half inhibition concentrations (IC$_{50}$) of 39.5 nM and 58.2 nM, respectively.

Next, PET/CT imaging studies were performed in nude mice bearing PC3-PIP tumor xenografts (PSMA-negative tumors) injected intravenously with $^{86}$Y-PSMA-617, $^{86}$Y-PSMA-C12, or $^{86}$Y-PSMA-PhC18 and scanned up to 72 h post injection. Results are shown in FIGS. 4A-4C. In FIG. 4C, the hydrophobic compound $^{86}$Y-PSMA-PhC18 shows prolonged blood circulation and minimal renal clearance. Notably tumor uptake and retention are significantly improved compared to $^{86}$Y-PSMA-617 (FIG. 4A) and $^{86}$Y-PSMA-C12 (FIG. 4B).

Figure 5:
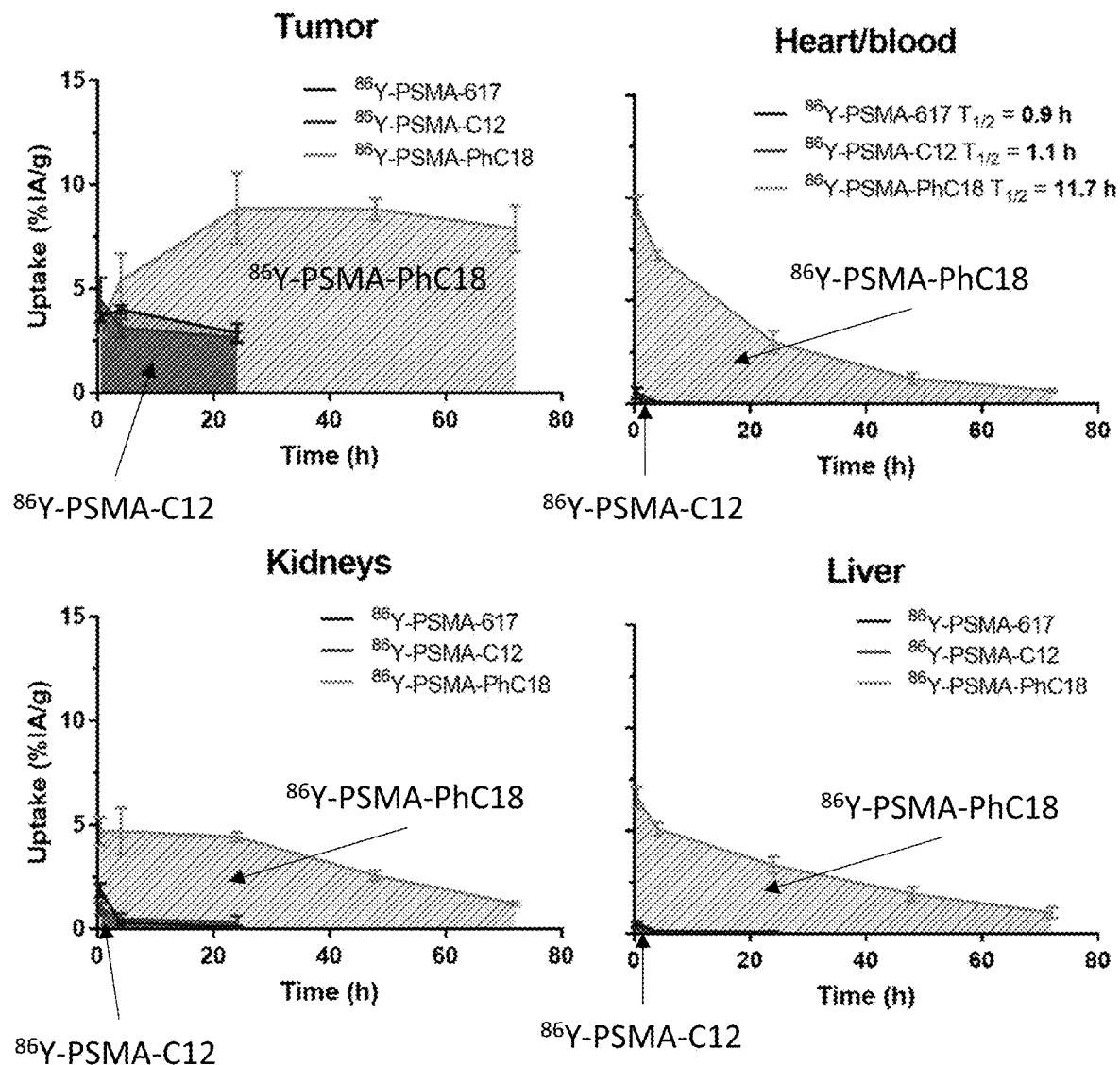
FIG. 5 shows a region of interest analysis (biodistribution analysis) of the PET/CT images in nude mice bearing PC3-PIP tumor xenografts injected intravenously with $^{86}$Y-PSMA-617, $^{86}$Y-PSMA-C12, or $^{86}$Y-PSMA-PhC18 and scanned up to 72 h post injection. $^{86}$Y-PSMA-PhC18 shows prolonged blood circulation with an 11.7 half-life and minimal renal clearance. $^{86}$Y-PSMA-PhC18 tumor uptake plateau at 24 h post injection.

A region of interest analysis was then performed on the PC3-PIP tumor xenografts injected intravenously with $^{86}$Y-PSMA-617, $^{86}$Y-PSMA-C12, or $^{86}$Y-PSMA-PhC18 and scanned up to 72 h post injection. As seen in FIG. 5, $^{86}$Y-PSMA-PhC18 shows prolonged blood circulation with an 11.7 h half-life and minimal renal clearance. $^{86}$Y-PSMA-PhC18 tumor uptake plateaus at 24 h post injection (p.i.).

Figure 6:
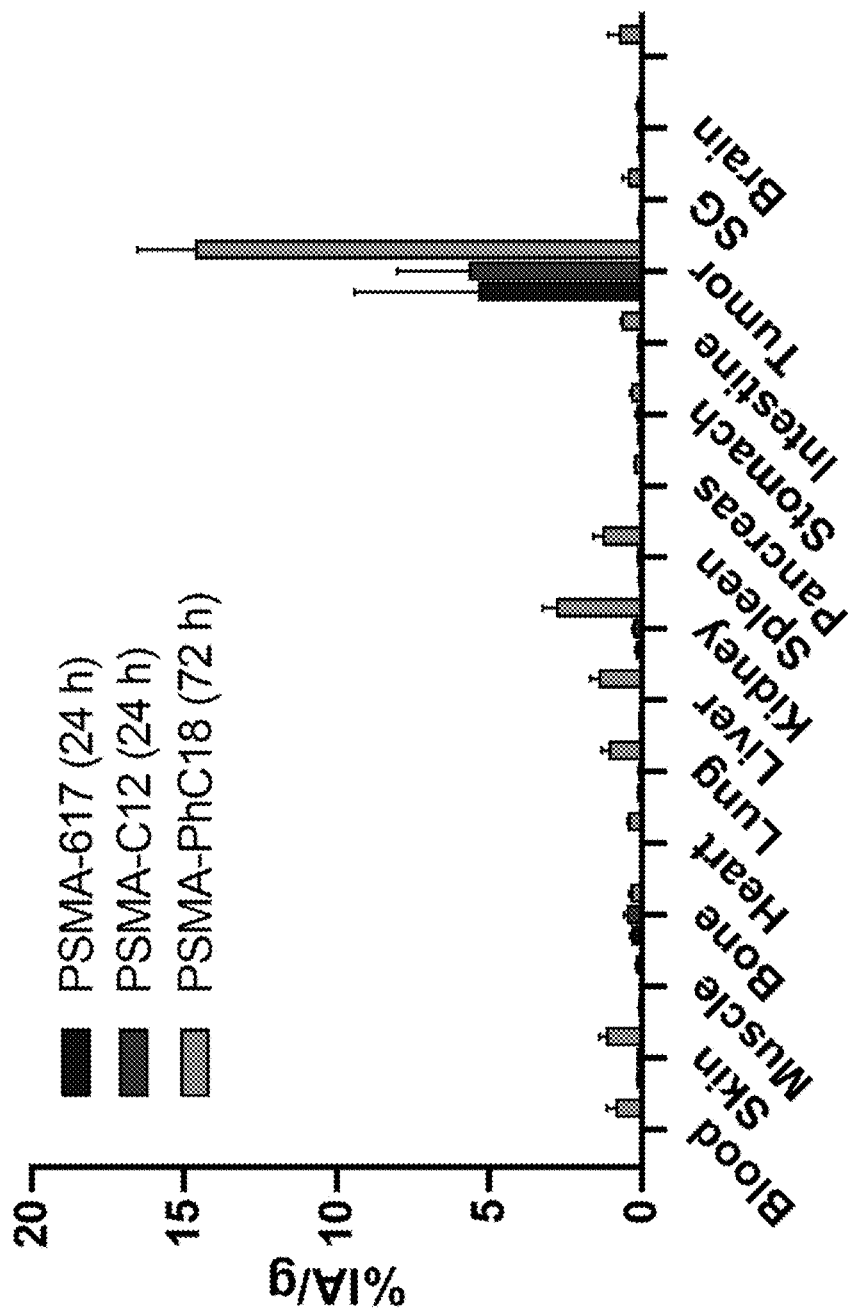
FIG. 6 shows ex vivo biodistribution following the last imaging timepoint at 24 h p.i. for PC3-PIP mice injected intravenously with $^{86}$Y-PSMA-617, $^{86}$Y-PSMA-C12, and at 72 h p.i. in mice administered $^{86}$Y-PSMA-PhC18.

Next, an ex vivo biodistribution analysis was performed following the last imaging timepoint at 24 h p.i. for PC3-PIP mice injected intravenously with ⁸⁶Y-PSMA-617 and ⁸⁶Y-PSMA-C12 and at 72 h p.i. in mice administered ⁸⁶Y-PSMA-PhC18. As shown in FIG. 6, at the time of biodistribution, the tumor shows the highest uptake of all analysed tissues for all three compounds. ⁸⁶Y-PSMA-617 displayed three-fold higher tumor uptake at a much later timepoint compared to the hydrophilic compounds ⁸⁶Y-PSMA-617 and ⁸⁶Y-PSMA-C12.

Next, PET/CT imaging studies were performed in nude mice bearing LNCap tumor xenografts with lower PSMA expression. The mice were injected intravenously with ⁸⁶Y-PSMA-617, ⁸⁶Y-PSMA-C12, or ⁸⁶Y-PSMA-PhC18 and scanned up to 72 h p.i. Results are shown in FIGS. 7A-7C. As seen in FIG. 7C, the more hydrophobic compound ⁸⁶Y-PSMA-PhC18 shows prolonged blood circulation and minimal renal clearance compared to the other two compounds. Tumor uptake and retention of ⁸⁶Y-PSMA-PhC18 are significantly improved compared to ⁸⁶Y-PSMA-617.

Figure 8:
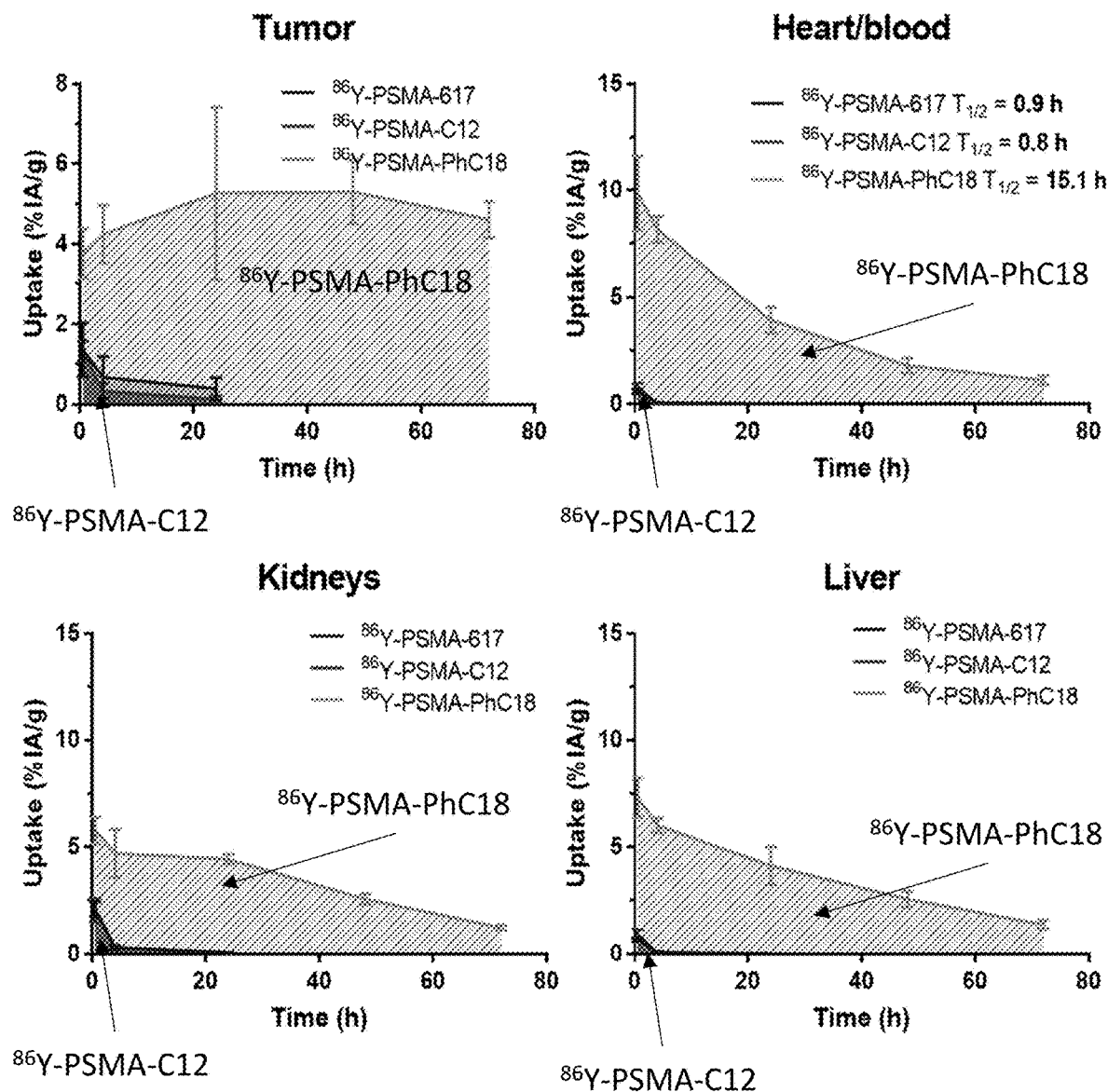
FIG. 8 shows a region of interest analysis (biodistribution analysis) of the PET/CT images in nude mice bearing LNCap tumor xenografts injected intravenously with $^{86}$Y-PSMA-617, $^{86}$Y-PSMA-C12, or $^{86}$Y-PSMA-PhC18 and scanned up to 72 h post injection.

Finally, a region of interest analysis was then performed on the PET/CT images in nude mice bearing LNCap tumor xenografts injected intravenously with ⁸⁶Y-PSMA-617, ⁸⁶Y-PSMA-C12, or ⁸⁶Y-PSMA-PhC18 and scanned up to 72 h post injection. As seen in FIG. 8, ⁸⁶Y-PSMA-PhC18 shows prolonged blood circulation with an 15.1 h half-life and minimal renal clearance. ⁸⁶Y-PSMA-PhC18 tumor uptake plateaued at 24 h p.i. and was five times higher at 72 h p.i. than that of ⁸⁶Y-PSMA-617 and ⁸⁶Y-PSMA-C12 at 24 h p.i. Steady clearance from normal organs was observed for ⁸⁶Y-PSMA-PhC18.

Other embodiments and uses of the invention will be apparent to those skilled in the art from consideration from the specification and practice of the invention disclosed herein. The invention is not confined to the specific reagents, formulations, reaction conditions, etc., herein illustrated and described, but embraces such modified forms thereof as come within the scope of the following claims.

The invention claimed is:

1. A theranostic agent having the formula:

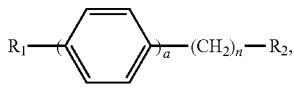

or a complex, anion or salt thereof, wherein:
$R_1$ comprises a chelating moiety;
a is 1;
n is 17; and
$R_2$ comprises a prostate specific membrane antigen (PSMA)-targeting moiety, wherein the theranostic agent has the formula:

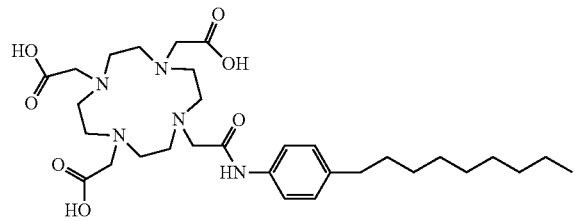

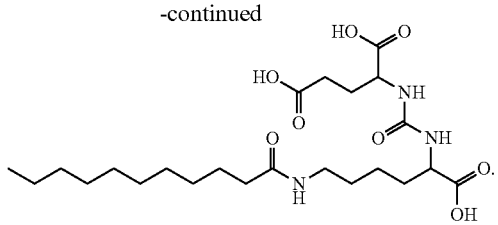

2. The theranostic agent of claim 1, wherein the chelating moiety is chelated to a metal atom in the form of a metal cation.

3. The theranostic agent of claim 2, wherein the chelating moiety is anionic and selected such that the theranostic agent as a whole is electrically neutral.

4. The theranostic agent of claim 2, wherein the metal atom is a positron or single photon emitting metal isotope, or an alpha, beta, or Auger emitting metal isotope.

5. The theranostic agent of claim 4, wherein the metal atom is a positron or single photon emitting metal isotope.

6. The theranostic agent of claim 5, wherein the metal isotope is selected from the group consisting of Ga-66, Cu-64, Y-86, Co-55, Zr-89, Sr-83, Mn-52, As-72, Sc-44, Sc-43, Ti-45, Tb-152, La-132, La-133, Ce-134, Ga-67, In-111, or Sm-153, Lu-177 or Tc-99m.

7. The theranostic agent of claim 4, wherein the metal atom is an alpha, beta or Auger emitting metal isotope.

8. The theranostic agent of claim 7, wherein the metal isotope is selected from the group consisting of Lu-177, Y-90, Ho-166, Re-186, Re-188, Cu-67, Au-199, Rh-105, Ra-223, Ac-225, As-211, Pb-212, Sc-47, Sm-153, Tb-161, Tb-149, Bi-213, Bi-212, or Th-227.

9. A composition comprising the theranostic agent of claim 1 and a pharmaceutically acceptable carrier.

10. A method for treating cancer associated with increased PSMA expression in a subject, comprising administering to the subject a therapeutically effective amount of the composition of claim 9,
wherein the theranostic agent comprises a metal atom chelated to the chelating moiety, and wherein the metal atom is an alpha, beta, or Auger emitting metal isotope, whereby the cancer is successfully treated in the subject.

11. A method for detecting or imaging one or more cancer cells associated with increased PSMA expression in a biological sample, comprising:
(a) contacting a biological sample with the theranostic agent of claim 1, wherein the theranostic agent comprises a metal atom chelated to the chelating moiety, and wherein the metal atom is a positron or single photon emitting metal isotope, whereby the theranostic agent is differentially bound to the cancer cells within the biological sample; and
(b) identifying individual cells or regions within the biological sample that are emitting signals characteristic of the metal isotope, whereby one or more cancer cells are detected and/or imaged.

* * * * *